US011317873B2

(12) United States Patent
Yamada et al.

(10) Patent No.: US 11,317,873 B2
(45) Date of Patent: May 3, 2022

(54) BIOLOGICAL ANALYSIS DEVICE, BIOLOGICAL ANALYSIS METHOD, AND PROGRAM

(71) Applicant: SEIKO EPSON CORPORATION, Tokyo (JP)

(72) Inventors: Kohei Yamada, Shiojiri (JP); Ayae Sawado, Kai (JP); Akiko Yamada, Shiojiri (JP); Megumi Enari, Shiojiri (JP); Yuta Machida, Chino (JP); Akira Ikeda, Chino (JP); Masayasu Fukuoka, Shiojiri (JP); Akira Kitahara, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 258 days.

(21) Appl. No.: 15/998,545

(22) Filed: Aug. 16, 2018

(65) Prior Publication Data
US 2019/0053767 A1    Feb. 21, 2019

(30) Foreign Application Priority Data

Aug. 16, 2017 (JP) ............................. JP2017-157161
May 31, 2018 (JP) ............................. JP2018-104933

(51) Int. Cl.
*A61B 5/00* (2006.01)
*A61B 5/021* (2006.01)
(Continued)

(52) U.S. Cl.
CPC ............ *A61B 5/7278* (2013.01); *A61B 5/021* (2013.01); *A61B 5/0261* (2013.01);
(Continued)

(58) Field of Classification Search
CPC ...... A61B 5/7278; A61B 5/021; A61B 5/1075; A61B 5/02108; A61B 5/0261; A61B 5/02007
See application file for complete search history.

(56) References Cited

U.S. PATENT DOCUMENTS

| 5,913,826 A | 6/1999 | Blank |
| 2002/0002339 A1 | 1/2002 | Sugo et al. |

(Continued)

FOREIGN PATENT DOCUMENTS

| JP | 2001-321347 A | 11/2001 |
| JP | 2004154231 A * | 3/2004 |

(Continued)

OTHER PUBLICATIONS

Masaki Goma et al. "The Development of Small Laser Doppler Blood Flow Sensor". Pioneer R&D, vol. 21, No. 1, 2012, pp. 30-36.

(Continued)

*Primary Examiner* — Joseph M Santos Rodriguez
*Assistant Examiner* — Kaitlyn E Selmer
(74) *Attorney, Agent, or Firm* — Oliff PLC

(57) ABSTRACT

A biological analysis device includes an average blood pressure calculation unit that calculates an average blood pressure index related to an average blood pressure of a biological body in accordance with a blood vessel diameter index related to a blood vessel diameter of the biological body and a blood flow index related to a blood flow of the biological body and calculated from an intensity spectrum related to a frequency of light reflected and received from an inside of the biological body through radiation of a laser beam.

14 Claims, 10 Drawing Sheets

(51) Int. Cl.
*A61B 5/026* (2006.01)
*A61B 5/107* (2006.01)
*A61B 5/02* (2006.01)

(52) U.S. Cl.
CPC ........ *A61B 5/02108* (2013.01); *A61B 5/1075* (2013.01); *A61B 5/02007* (2013.01)

(56) References Cited

U.S. PATENT DOCUMENTS

| | | | |
|---|---|---|---|
| 2004/0024295 A1* | 2/2004 | Cook | A61B 5/14535 600/310 |
| 2011/0319775 A1* | 12/2011 | Fujii | A61B 3/1233 600/504 |
| 2015/0018693 A1 | 1/2015 | Mestha et al. | |
| 2015/0216458 A1 | 8/2015 | Kasahara et al. | |
| 2016/0174854 A1* | 6/2016 | Nishida | A61B 5/02007 600/480 |
| 2018/0293797 A1* | 10/2018 | Rana | G06T 19/006 |
| 2019/0090818 A1* | 3/2019 | Nakajima | A61B 5/746 |
| 2019/0380598 A1 | 12/2019 | Higuchi | |
| 2020/0276380 A1 | 9/2020 | Maierhofer et al. | |

FOREIGN PATENT DOCUMENTS

| | | | |
|---|---|---|---|
| JP | 2004-154231 A | | 6/2004 |
| JP | 2004154231 A | * | 6/2004 |
| JP | 2008-018035 A | | 1/2008 |
| JP | 2016-146958 A | | 8/2016 |
| JP | 2016-150065 A | | 8/2016 |
| JP | 2019-033902 A | | 3/2019 |
| WO | 2012/142455 A2 | | 10/2012 |
| WO | 2015/199159 A1 | | 12/2015 |
| WO | 2016/130083 A1 | | 8/2016 |
| WO | WO 2016130083 A1 | * | 8/2016 |

OTHER PUBLICATIONS

U.S. Appl. No. 16/103,968, filed Aug. 16, 2018 in the name of Megumi Enari et al.
U.S. Appl. No. 15/998,546, filed Aug. 16, 2018 in the name of Ayae Sawado et al.
Sep. 8, 2020 Office Action issued in U.S. Appl. No. 15/998,546.
May 12, 2021 Notice of Allowance issued in U.S. Appl. No. 15/998,546.
Jun. 25, 2021 Office Action issued in U.S. Appl. No. 16/103,968.
Dec. 30, 2020 Office Action issued in U.S. Appl. No. 15/998,546.
Jan. 11, 2021 U.S. Office Action issued in U.S. Appl. No. 16/103,968.

* cited by examiner

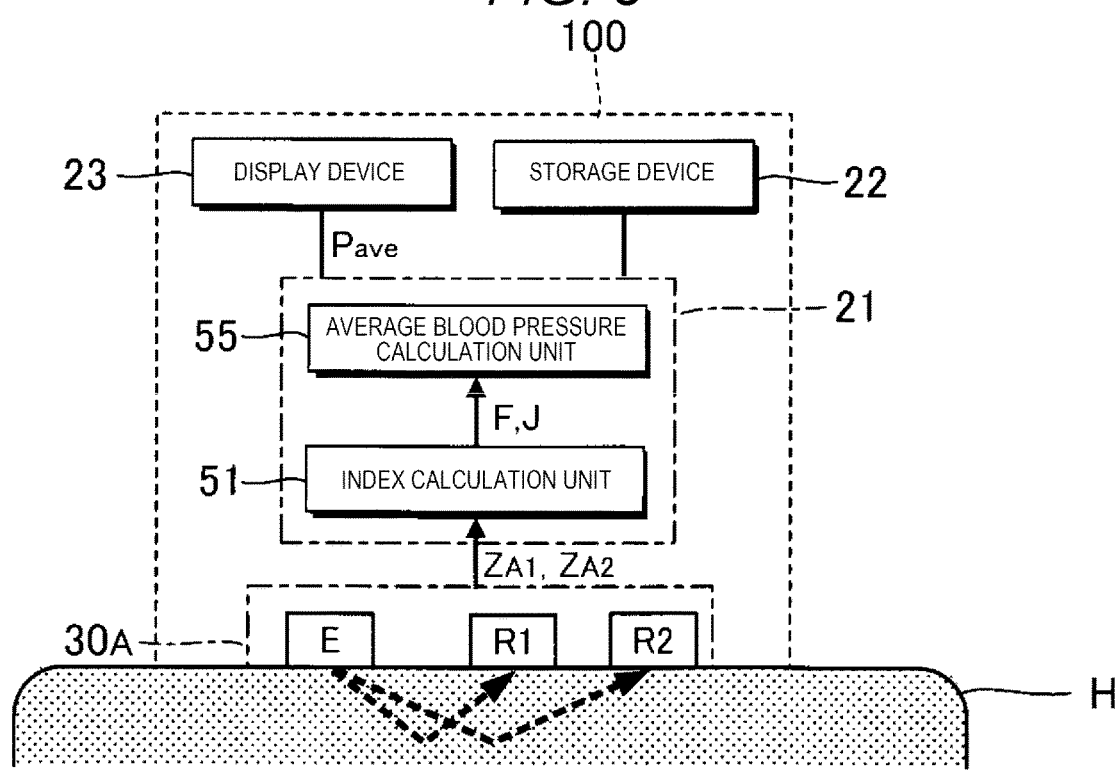

BIOLOGICAL ANALYSIS DEVICE, BIOLOGICAL ANALYSIS METHOD, AND PROGRAM

BACKGROUND

1. Technical Field

The present invention relates to a technology for analyzing a biological body.

2. Related Art

Various measurement technologies for analyzing biological information such as blood pressures have been proposed in the related art. For example, JP-T-2015-199159 discloses a blood pressure measurement device that measures a blood pressure in a state in which a measurement target part is pressed on a pressure sensor. Specifically, when a contact pressure detected by the pressure sensor is predetermined value, a blood pressure is measured using an optical blood flow sensor.

In the technology of JP-T-2015-199159, an error caused due to a difference in the contact pressure can occur.

SUMMARY

A biological analysis device according to a preferred aspect of the invention includes an average blood pressure calculation unit that calculates an average blood pressure index related to an average blood pressure of a biological body in accordance with a blood vessel diameter index related to a blood vessel diameter of the biological body and a blood flow index related to a blood flow of the biological body and calculated from an intensity spectrum related to a frequency of light reflected and received from an inside of the biological body through radiation of a laser beam.

A biological analysis method according to a preferred aspect of the invention includes calculating an average blood pressure index related to an average blood pressure of a biological body in accordance with a blood vessel diameter index related to a blood vessel diameter of the biological body and a blood flow index related to a blood flow of the biological body and calculated from an intensity spectrum related to a frequency of light reflected and received from an inside of the biological body through radiation of a laser beam.

A program according to a preferred aspect of the invention causes a computer to function as an average blood pressure calculation unit that calculates an average blood pressure index related to an average blood pressure of a biological body in accordance with a blood vessel diameter index related to a blood vessel diameter of the biological body and a blood flow index related to a blood flow of the biological body and calculated from an intensity spectrum related to a frequency of light reflected and received from an inside of the biological body through radiation of a laser beam.

BRIEF DESCRIPTION OF THE DRAWINGS

The invention will be described with reference to the accompanying drawings, wherein like numbers reference like elements.

FIG. 5 is a diagram illustrating a configuration in which a function of the biological analysis device is focused on.

FIG. 8 is a diagram illustrating a configuration of a biological analysis device according to a third embodiment.

FIG. 9 is a table illustrating quality of an SN ratio (signal-to-noise ratio) in a frequency bandwidth used in calculation of a blood flow index in a detection signal and quality of an SN ratio in a frequency bandwidth used in calculation of an absorbance index in a detection signal in a plurality of cases in which a distance between the light-emitting unit and the light-receiving unit is changed.

DESCRIPTION OF EXEMPLARY EMBODIMENTS

First Embodiment

Figure 1:
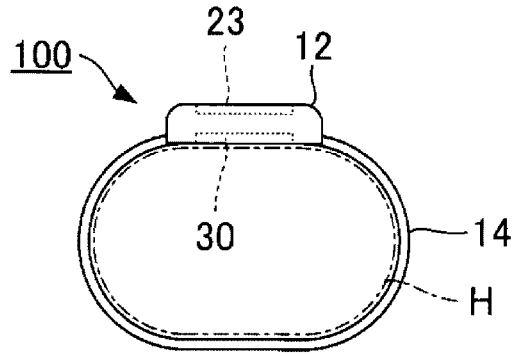
FIG. 1 is a side view illustrating a biological analysis device according to a first embodiment of the invention.

FIG. 1 is a side view illustrating a biological analysis device 100 according to a first embodiment of the invention. The biological analysis device 100 is a measurement instrument that measures biological information of a subject in a non-invasive manner. The biological analysis device 100 according to the first embodiment measures an average blood pressure Pave of a specific part (hereinafter referred to as a "measurement region") H of the body of a subject (user) as biological information. In the following description, a wrist or an upper arm of the subject is exemplified as the measurement region H.

Figure 2:
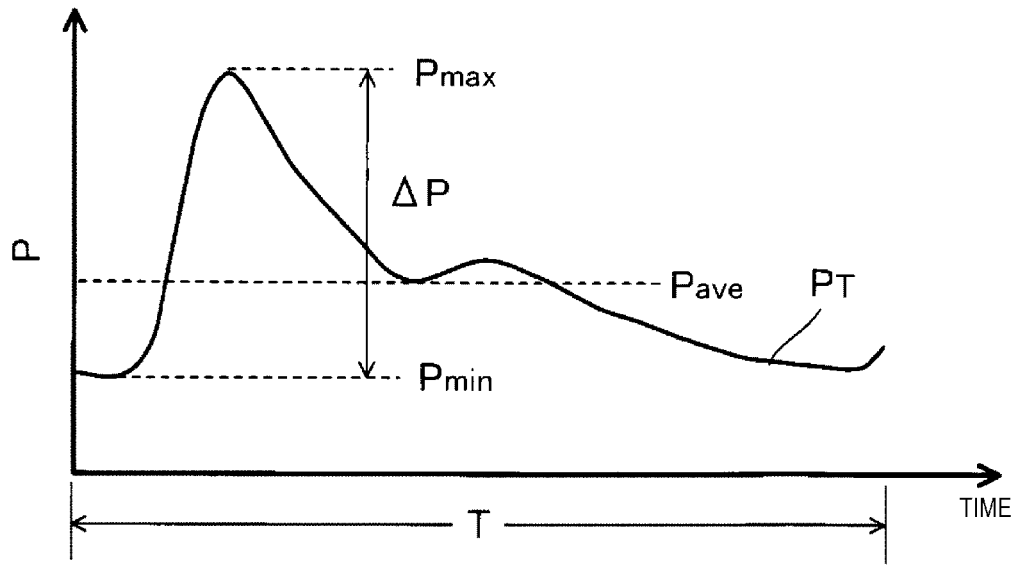
FIG. 2 is a graph illustrating a temporal change in a blood pressure.

FIG. 2 is a graph illustrating a temporal change PT in a blood pressure P. In the first embodiment, an average blood pressure Pave during an analysis period (about 0.5 to 1 second) T equivalent to one beat is measured. A time length of the analysis period T is not limited to one beat. In FIG. 2, Pmax is a systolic blood pressure (maximum pressure) and Pmin is a diastolic blood pressure (minimum pressure). ΔP is a difference (that is, a pulse pressure) between the systolic blood pressure Pmax and the diastolic blood pressure Pmin.

Figure 3:
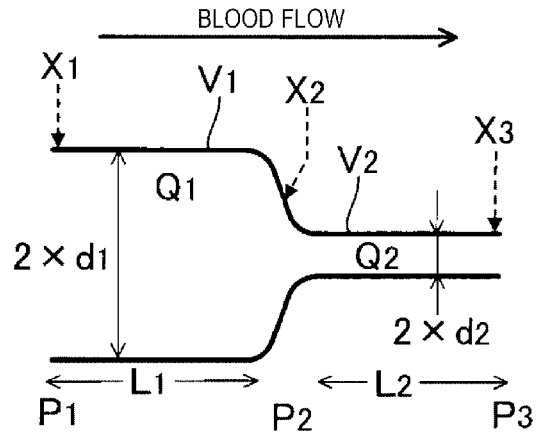
FIG. 3 is a schematic diagram illustrating a blood vessel of an arm.

FIG. 3 is a schematic diagram illustrating a blood vessel of an arm. FIG. 3 illustrates an artery (for example, radial artery) V1 and an arteriole (for example, a finger artery) V2 connected to the artery V1. As exemplified in FIG. 3, a site X1 is a predetermined site in the artery V1, a site X2 is a site between the artery V1 and an arteriole V2, and a site X3 is a site of an erasure of the arteriole V2. That is, the site X1 is closer to a heart than the site X3.

A relation among a blood pressure P1 at the site X1 in the artery V1, a blood pressure P2 at the site X2 between the artery V1 and the arteriole V2, and a blood pressure P3 at the site X3 of the erasure of the arteriole V2 is expressed in Expressions (1) and (2) below using the Hagen-Poiseuille law. A sign L1 in Expression (1) is the length of the artery V1, a sign Q1 is a blood flow of the artery V1, and a sign d1 is a blood vessel diameter (radius) of the artery V1. A sign L2 in Expression (2) is the length of the arteriole V2, a sign Q2 is a blood flow of the arteriole V2, and a sign d2 is a blood vessel diameter (radius) of the arteriole V2. A sign ρ in Expressions (1) and (2) is blood density.

$$P_1 - P_2 = \frac{8\rho L_1 Q_1}{\pi d_1^4} \quad (1)$$

$$P_2 - P_3 = \frac{8\rho L_2 Q_2}{\pi d_2^4} \quad (2)$$

An amount of change (that is, P1−P3) of a blood pressure from the site X1 to the site X3 is expressed in Expression (3) below using Expressions (1) and (2).

$$P_1 - P_3 = \frac{8\rho L_1 Q_1}{\pi d_1^4} + \frac{8\rho L_2 Q_2}{\pi d_2^4} \quad (3)$$

Figure 4:
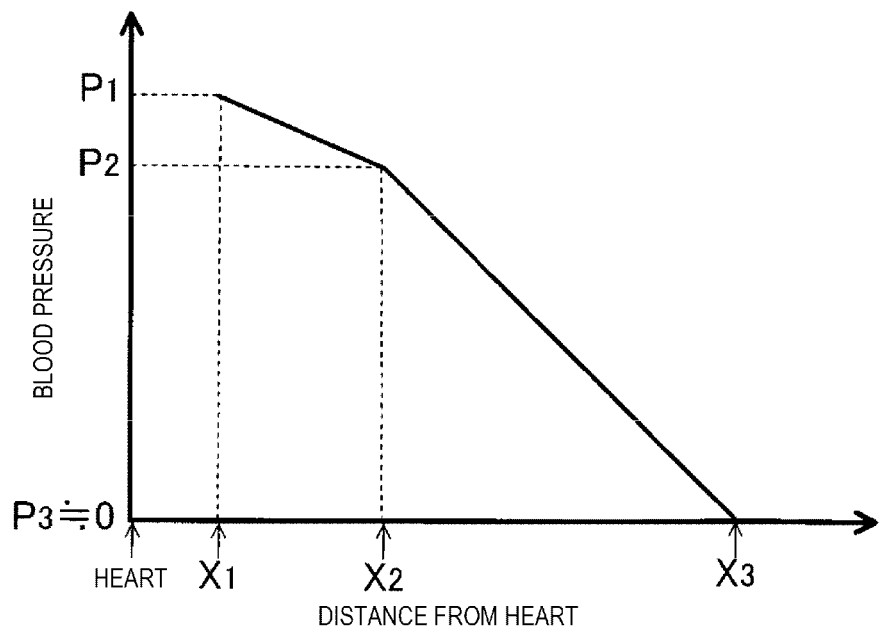
FIG. 4 is a graph illustrating a relation between a distance from a heart to a specific part of a blood vessel and an average blood pressure of the specific part.

FIG. 4 is a graph illustrating a relation between a distance from a heart to a specific part on a blood vessel and a blood pressure of the specific part. As understood from FIG. 4, the amount of change (that is, P1−P2) of the blood pressure from the site X1 to the site X2 tends to be sufficiently smaller than an amount of change (that is, P2−P3) of a blood pressure from the site X2 to the site X3. Specifically, the amount of change (P1−P2) is about 1 to 5 mmHg and the amount of change (P2−P3) is about 100 mmHg. The blood pressure P3 at the site X3 of the erasure of the arteriole V2 is known to be very small (for example, a few mmHg). Accordingly, when the blood pressure P3 of the amount of change (P1−P2) is assumed to be 0 mmHg, Expression (4) below is derived from Expression (3).

$$P_1 = \frac{8\rho L_2 Q_2}{\pi d_2^4} \quad (4)$$

Since an individual difference in the blood density ρ is small, the blood density ρ can be set to a predetermined value (for example, 1070 kg/m³). The distance L2 can be set to a predetermined value estimated from a height, a sex, and the like of a subject. That is, by calculating a blood flow Q2 and a blood vessel diameter d2 of the arteriole V2, the blood pressure P1 of the artery can be calculated.

The biological analysis device 100 in FIG. 1 is mounted on the measurement region H (the upper arm or the wrist) The biological analysis device 100 according to the first embodiment is a wrist-watch type portable device including a casing 12 and a belt 14. The biological analysis device 100 is mounted on the body of the subject by winding the belt 14 around the measurement region H. In the first embodiment, the biological analysis device 100 is mounted at a position at which an arteriole is inside the measurement region H.

Figure 5:
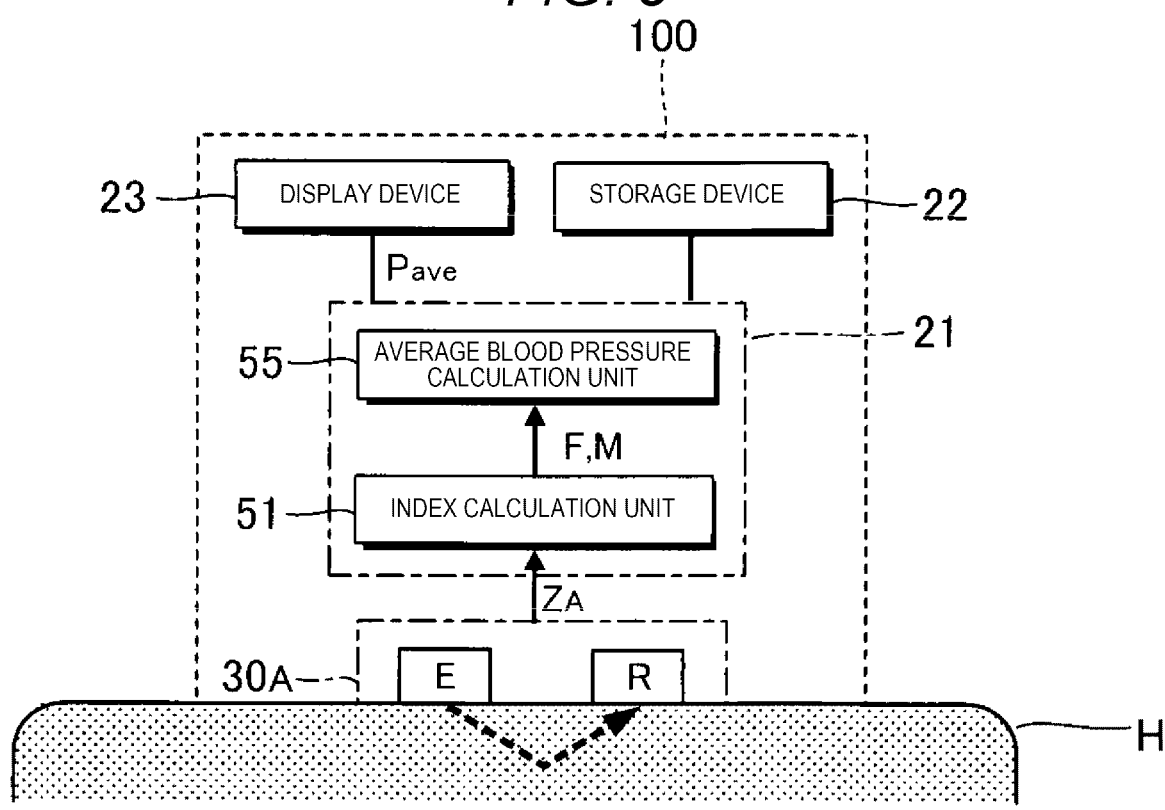

FIG. 5 is a diagram illustrating a configuration in which a function of the biological analysis device 100 is focused on. The biological analysis device 100 according to the first embodiment includes a control device 21, a storage device 22, a display device 23, and a detection device 30A. The control device 21 and the storage device 22 are installed inside the casing 12.

The display device 23 (for example, a liquid crystal panel) is installed on, for example, a surface of the casing 12 opposite to the measurement region H, as illustrated in FIG. 1. The display device 23 displays various images including a measurement result under the control of the control device 21.

The detection device 30A is an optical sensor module that generates a detection signal ZA in accordance with a state of the measurement region H. Specifically, the detection device 30A includes a light-emitting unit E and a light-receiving unit R. The light-emitting unit E and the light-receiving unit R are installed at, for example, positions (generally, a surface in contact with the measurement region H) of the casing 12 facing the measurement region H.

The light-emitting unit E is a light source that radiates light to the measurement region H. The light-emitting unit E according to the first embodiment radiates a coherent laser beam to the measurement region H (biological body) with a narrowband. For example, a light-emitting element such as a vertical cavity surface emitting LASER (VCSEL) that emits a laser beam by resonance in a resonator is used appropriately as the light-emitting unit E. The light-emitting unit E according to the first embodiment radiates, for example, light with a predetermined wavelength (for example, 800 nm to 1300 nm) in a near infrared area to the measurement region H. The light-emitting unit E emits light under the control of the control device 21. The light emitted by the light-emitting unit E is not limited to the near infrared light.

Light incident on the measurement region H from the light-emitting unit E is repeatedly diffused and reflected while passing through the inside of the measurement region H to exit to the side of the casing 12. Specifically, the light passing through blood vessels inside the measurement region H and blood in the blood vessels exits from the measurement region H to the side of the casing 12.

The light-receiving unit R receives the laser beam reflected inside the measurement region H. Specifically, the light-receiving unit R generates a detection signal ZA indicating a light reception level of the light passing through the measurement region H. For example, a light-receiving element such as a photodiode (PD) that generates charges in accordance with the light reception intensity is used as the light-receiving unit R. Specifically, a light-receiving element in which a photoelectric conversion layer is formed of indium, gallium, and arsenic (InGaAs) having high sensitivity in a near infrared area is suitable as the light-receiving unit R. As understood from the above description, the detection device 30A according to the first embodiment is a reflective optical sensor in which the light-emitting unit E and the light-receiving unit R are located on side of the measurement region H. Here, a transmissive optical sensor in which the light-emitting unit E and the light-receiving unit R are located on opposite sides with the measurement region H interposed therebetween may be used as the detection device 30A. The detection device 30A includes, for example, a driving circuit that drives the light-emitting unit E by applying a driving current and output circuits (for example, an amplification circuit and an A/D converter) that perform amplification and A/D conversion on a signal output by the light-receiving unit R, but these circuits are not illustrated in FIG. 5.

The light arriving at the light-receiving unit R includes a component diffused and reflected from a tissue (a stationary tissue) stationary inside the measurement region H and a component diffused and reflected from an object (generally, a red blood cell) moving inside a blood vessel inside the measurement region H. The frequency of light before and after the diffusion and reflection from a stationary tissue is not changed. However, before and after diffusion and reflection from a red blood cell, the frequency of light is changed by an amount of change (hereinafter referred to as a "frequency shift amount" proportional to a movement speed (that is, a blood flow rate) of the red blood cell. That is, the light passing through the measurement region H and arriving at the light-receiving unit R contains a component that is changed (frequency-shifted) by the frequency shift amount with respect to the frequency of the light emitting the light-emitting unit E. The detection signal ZA supplied to the control device 21 is an optical beat signal in which the frequency shift by a blood flow inside the measurement region H is reflected.

The control device 21 is an arithmetic processing device such as a central processing unit (CPU) or a field-programmable gate array (FPGA) and controls the whole biological analysis device 100. The storage device 22 includes, for example, a nonvolatile semiconductor memory and stores a program to be executed by the control device 21 and various kinds of data to be used by the control device 21. A configuration in which functions of the control device 21 are distributed to a plurality of integrated circuits can be adopted or a configuration in which some or all of the functions of the control device 21 are realized by a dedicated electronic circuit can also be adopted. In FIG. 5, the control device 21 and the storage device 22 are illustrated as separate elements, but the control device 21 containing the storage device 22 can also be realized by, for example, an application specific integrated circuit (ASIC).

The control device 21 according to the first embodiment realizes a plurality of functions (an index calculation unit 51 and an average blood pressure calculation unit 55) of calculating the average blood pressure Pave from the detection signal ZA generated by the detection device 30A by executing a program stored in the storage device 22. Some of the functions of the control device 21 may be realized by a dedicated electronic circuit.

The index calculation unit 51 calculates the blood vessel diameter index and the blood flow index F of the measurement region H from the detection signal ZA generated by the detection device 30A. The blood vessel diameter index is an index related to a blood vessel diameter (and a cross-sectional area of a blood vessel) of a biological body. A blood mass is changed in conjunction with pulsation of a blood vessel diameter synchronized with a beat of a heart. That is, the blood mass index also correlates with a blood vessel diameter. In consideration of the foregoing correlation, in the first embodiment, the blood mass index M is exemplified as a blood vessel diameter index. The blood mass index M (so-called MASS value) is an index related to a blood mass (specifically, the number of red blood cells in a unit volume) of a biological body. On the other hand, the blood flow index F (so-called FLOW value) is an index related to a blood flow of a biological body (that is, a volume of blood moving in an artery in a unit time). The blood flow index F is paraphrased as an index related to a flood flow rate.

The index calculation unit 51 calculates an intensity spectrum from the detection signal ZA and calculates the blood mass index M and the blood flow index F from the intensity spectrum. The intensity spectrum is a distribution of an intensity (power or amplitude) G(f) of a signal component of the detection signal ZA at each frequency (Doppler frequency) on a frequency axis. In the calculation of the intensity spectrum, any known frequency analysis such as fast Fourier transform (FFT) can be adopted. The calculation of the intensity spectrum is executed repeatedly at a period shorter than the analysis period T.

The blood mass index M is expressed in Expression (5a) below. A sign $\langle I^2 \rangle$ in Expression (5a) is an average intensity over the whole bandwidth of the detection signal ZA or an intensity G(0) (that is, an intensity of a direct-current component) at 0 Hz in the intensity spectrum.

$$M = \frac{\int_{f_L}^{f_H} G(f)df}{\langle I^2 \rangle} \tag{5a}$$

As understood from Expression (5a), the blood mass index M is calculated by integrating the intensity G(f) of each frequency f in the intensity spectrum in a range between a lower limit fL and upper limit fH on the frequency axis. The lower limit fL is less than the upper value fH. The blood mass index M may be calculated by calculating Expression (5b) below in which an integral of Expression (5a) is replaced with a total sum ($\Sigma$). The sign $\Delta f$ in Expression (5b) is a bandwidth corresponding to one intensity G(f) on the frequency axis and is equivalent to a horizontal width of each rectangle when the intensity spectrum is approximated with a plurality of rectangles arranged on the frequency axis. The calculation of the blood mass index M is repeatedly executed at a period shorter than the analysis period T. As understood from the above description, the blood mass index M is calculated (specifically, the intensity of each frequency in the intensity spectrum is integrated in a predetermined frequency range) from an intensity spectrum related to the frequency of light reflected and received inside in a biological body by radiating a laser beam.

$$M = \frac{\sum_{f=f_L}^{f_H} \Delta f \cdot G(f)}{\langle I^2 \rangle} \quad (5b)$$

The blood flow index F is expressed in Expression (6a) below.

$$F = \frac{\int_{f_L}^{f_H} f \cdot G(f) df}{\langle I^2 \rangle} \quad (6a)$$

As understood from Expression (6a), the blood flow index F is calculated by integrating a product (f×G(f)) of the intensity G(f) of each frequency f in the intensity spectrum and the frequency f in a range between a lower limit fL and an upper limit fH on the frequency axis. Hereinafter, the product (f×G(f)) of the intensity G(f) of each frequency f in the intensity spectrum and the frequency f is referred to as a "frequency weighted intensity spectrum". The blood flow index F may be calculated by calculating Expression (6b) below in which an integral of Expression (6a) is replaced with a total sum (Σ). The blood flow index F is repeatedly calculated at a period shorter than the analysis period T. As understood from the above description, the blood flow index F is calculated (specifically, the product of the intensity of each frequency in the intensity spectrum and the frequency is integrated in a predetermined frequency range) from an intensity spectrum related to the frequency of light reflected and received inside in a biological body by radiating a laser beam.

$$F = \frac{\sum_{f=f_L}^{f_H} f \cdot \Delta f \cdot G(f)}{\langle I^2 \rangle} \quad (6b)$$

The average blood pressure calculation unit 55 in FIG. 5 calculates the average blood pressure Pave of the biological body in accordance with the blood mass index M and the blood flow index F calculated by the index calculation unit 51. Specifically, the average blood pressure calculation unit 55 calculates the average blood pressure Pave in accordance with an average value Mave obtained by averaging the blood mass indexes M during the analysis period T and an average value Fave obtained by averaging the blood flow indexes F during the analysis period T. The average value Mave is an average (for example, a simple average or a weighted average) of the plurality of blood mass indexes M calculated during the analysis period T. The average value Fave is an average (for example, a simple average or a weighted average) of the plurality of blood flow indexes F calculated during the analysis period T.

As described above, the blood mass index M correlates with a blood vessel diameter d. Specifically, a cubic root ($M^{1/3}$) of the blood mass index M is equivalent to the blood vessel diameter d2. The third power of the blood vessel diameter d2 is paraphrased to be equivalent to the blood mass index M. The blood flow index F is equivalent to a blood flow Q2. In consideration of the foregoing relation, Expression (4) described above is modified into Expression (7) below.

$$P_{ave} = K \times \frac{F_{ave}}{M_{ave}^{4/3}} \quad (7)$$

The average blood pressure calculation unit 55 according to the first embodiment calculates the average blood pressure Pave by calculation of Expression (7). A sign K is a coefficient determined in advance in accordance with the blood density ρ, a length L2 of an arteriole, and the like. As understood from Expression (7), the average blood pressure Pave is calculated in accordance with $F_{ave}/M_{ave}^{4/3}$. The coefficient K is set from an actually measured value of the average blood pressure Pave actually measured, for example, using a cuff or the like and a calculated value of $F_{ave}/M_{ave}^{4/3}$ of Expression (7) (for example, K=actually measured value/calculated value). The control device 21 causes the display device 23 to display the average blood pressure Pave calculated by the average blood pressure calculation unit 55.

Figure 6:
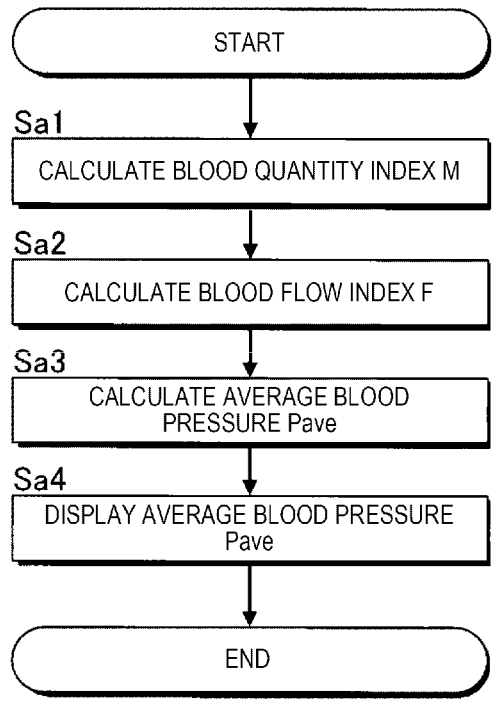
FIG. 6 is a flowchart illustrating a biological analysis process executed by a control device.

FIG. 6 is a flowchart illustrating a process (hereinafter referred to as a "biological analysis process") executed by the control device 21. The biological analysis process in FIG. 6 is executed during each analysis period T on the time axis. When the biological analysis process starts, the index calculation unit 51 calculates the blood mass index M at each of a plurality of time points within the analysis period T (Sa1). In the calculation of the blood mass index M, Expression (5a) or (5b) described above is used. Subsequently, the index calculation unit 51 calculates the blood flow index F at each of the plurality of time points within the analysis period T (Sa2). In the calculation of the blood flow index F, Expression (6a) or (6b) described above is used. The average blood pressure calculation unit 55 calculates the average blood pressure Pave in accordance with the blood mass index M and the blood flow index F calculated by the index calculation unit 51 (Sa3). The control device 21 causes the display device 23 to display the average blood pressure Pave calculated by the average blood pressure calculation unit 55 (Sa4). The order of the calculation (Sa1) of the blood mass index M and the calculation (Sa2) of the blood flow index F may be reversed. By executing the above-described biological analysis process during each analysis period T, a time series of the plurality of average blood pressures Pave (that is, a temporal change in the average blood pressure Pave) are calculated.

Figure 7:
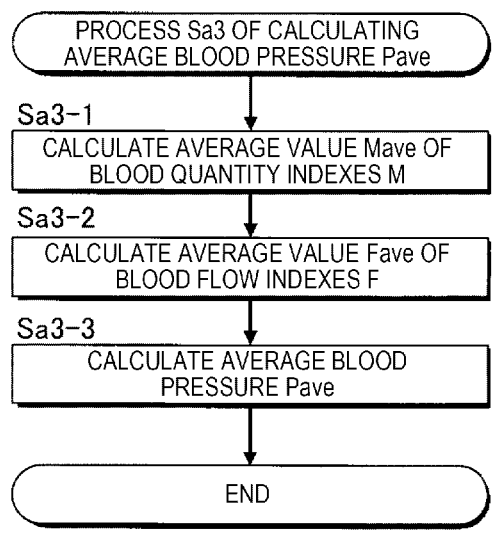
FIG. 7 is a flowchart illustrating specific content of a process of calculating an average blood pressure.

FIG. 7 is a flowchart illustrating specific content of a process Sa3 of calculating the average blood pressure Pave. The average blood pressure calculation unit 55 calculates the average value Mave obtained by averaging the blood mass index M during the analysis period T (Sa3-1). The average blood pressure calculation unit 55 calculates the average value Fave obtained by averaging the blood flow indexes F during the analysis period T (Sa3-2). Then, the average blood pressure calculation unit 55 calculates the average blood pressure Pave in accordance with the average value Mave and the average value Fave (Sa3-3). Specifically, the average blood pressure Pave is calculated in accordance with Fave/Mave$^{4/3}$. The order of the calculation (Sa3-1) of the average value Mave and the calculation (Sa3-2) of the average value Fave may be reversed.

As described above, according to the first embodiment, the average blood pressure Pave is calculated in accordance with the blood vessel diameter index (the blood mass index M) and the blood flow index F. Here, for example, in a configuration in which a biological body is compressed in calculation of an average blood pressure (for example, a configuration in which an average blood pressure is calculated using a cuff or the like), an error caused due to a difference in a pressure force can occur. However, according to the first embodiment, since the average blood pressure Pave is calculated in accordance with the blood vessel diameter index (the blood mass index M) and the blood flow index F, it is unnecessary to compress a biological body. Furthermore, an error caused due to a difference in a pressure force can be reduced and the average blood pressure Pave can be calculated with high precision.

Incidentally, in calculation of the blood flow index F, a blood flow rate sensor that radiates an ultrasonic wave to a biological body can also be used. However, when an ultrasonic wave radiation type of blood flow rate sensor is used, a skin thickness of a measurement region or the flow index F has an influence on a condition that a radiation surface of an ultrasonic wave comes into contact with a biological body (the degree or a pressure of adherence). It is difficult to actually specify an index related to a blood pressure (for example, an average blood pressure) with high precision. When the ultrasonic wave radiation type of blood flow rate sensor is used, there is also the problem that the size of a biological analysis device increases. According to the first embodiment, however, since a laser beam is used in calculation of the blood flow index F, the influence of a skin thickness or the like can be reduced and the average blood pressure Pave can be measured with higher precision than in a case in which an ultrasonic wave radiation type blood flow rate sensor is used. It is possible to miniaturize the biological analysis device 100.

Second Embodiment

A second embodiment of the invention will be described. Elements similar to those of the first embodiment in operations or functions in each embodiment to be exemplified below, the reference numerals used in the description of the first embodiment are applied, and a detailed description of each element will be appropriately omitted.

Absorbance Abs of blood is changed in conjunction with pulsation of a blood vessel diameter. That is, the absorbance Abs correlates with a blood vessel diameter. Specifically, a relation between the absorbance Abs and the blood vessel diameter d is expressed in Expression (8) below. A sign ε in Expression (8) is a molar absorbance coefficient and a sign c is red blood cell density. From the foregoing reason, according to the second embodiment, an index J related to the absorbance Abs of a biological body (hereinafter referred to as an "absorbance index") is exemplified as a blood vessel diameter index.

$$Abs = \varepsilon c d \qquad (8)$$

The index calculation unit 51 according to the second embodiment calculates the absorbance index J and a blood flow index F similar to that of the first embodiment. The absorbance Abs is expressed in Expression (9) below. A sign I in Expression (9) is an intensity of a signal component of the detection signal ZA and a sign I0 is an intensity of light incident on a measurement region (an intensity of light emitted from the light-emitting unit E). Expression (10) is derived from Expressions (8) and (9).

$$Abs = -\log(I/I_0) \qquad (9)$$

$$d = \frac{-\log(I/I_0)}{\varepsilon c} \qquad (10)$$

The molar absorbance coefficient ε and the red blood cell density c can be set to predetermined values. That is, by calculating a common logarithm ($\log(I/I0)$) of a ratio of the intensity I0 and the intensity I, it is possible to calculate the blood vessel diameter d. Accordingly, the index calculation unit 51 according to the second embodiment calculates the common logarithm ($\log(I/I0)$) of the ratio of the intensity I0 and the intensity I as the absorbance index J. The intensity I0 is set to a predetermined value and the intensity I is calculated from a photoelectric volume pulse wave indicating a light reception level of light received from a biological body (the measurement region H). That is, the absorbance index J is calculated from the photoelectric volume pulse wave. The photoelectric volume pulse wave is generated from the detection signal ZA generated by the detection device 30A. For example, the photoelectric volume pulse wave is generated through a filtering process of suppressing a high-frequency component of the detection signal ZA output by the detection device 30A and an amplification process of amplifying a signal subjected to the filtering process. The blood flow index F is calculated in accordance with a method similar to that of the first embodiment.

The average blood pressure calculation unit 55 according to the second embodiment calculates the average blood pressure Pave from the absorbance index J and the blood flow index F calculated by the index calculation unit 51. Specifically, the average blood pressure calculation unit 55 calculates the average blood pressure Pave in accordance with the average value Jave obtained by averaging the absorbance indexes J during the analysis period T and the average value Fave obtained by averaging the blood flow indexes F during the analysis period T. As described above, the absorbance index J correlates with the blood vessel diameter d2 and the blood flow index F is equivalent to the blood flow Q2. In consideration of the foregoing relation, Expression (11) is derived from Expressions (4) and (10) described above. The average blood pressure calculation unit 55 calculates the average blood pressure Pave by calculating Expression (11). A sign K is a coefficient determined in advance in accordance with the blood density ρ, the length L2 of an arteriole, and the like. The coefficient K is a coefficient determined in advance in accordance with the molar absorbance coefficient ε, the red blood cell c, the blood density ρ, the length L2 of an arteriole, and the like. As understood from Expression (11), the average blood pressure Pave according to the second embodiment is in accordance with Fave/Jave$^4$. The coefficient K is set from, for example, a value actually measured using a cuff or the like and the calculation of Fave/Jave$^4$ in Expression (11) (for example, K=actually measured value/calculated value).

$$P_{ave} = K \times \frac{F_{ave}}{J_{ave}^4} \quad (11)$$

Content of the biological analysis process according to the second embodiment is similar to that of the first embodiment exemplified in FIG. 6. However, in step Sa1 of FIG. 6, the index calculation unit 51 calculates the absorbance index J instead of the blood mass index M. In step Sa3-1 of FIG. 7, the average blood pressure calculation unit 55 calculates the average value Jave of the absorbance indexes J instead of the average value Mave of the blood mass indexes M.

In the second embodiment, advantages similar to those of the first embodiment are obtained. In the second embodiment, in particular, since the absorbance index J calculated from the photoelectric volume pulse wave indicating a light reception level of light received from a biological body is used as the blood vessel diameter index, a processing load for calculating the blood vessel diameter index is reduced further than in the configuration of the first embodiment in which the blood mass index M calculated from the intensity spectrum is used as the blood vessel diameter index.

Third Embodiment

According to a third embodiment, the average blood pressure Pave is calculated in accordance with the absorbance index J and the blood mass index F, as in the second embodiment. However, while the detection signal ZA generated by the common light-receiving unit R is used in the calculation of the absorbance index J and the calculation of the blood flow index F in the second embodiment, a detection signal Z generated by a separate light-receiving unit R is used in calculation of the absorbance index J and the calculation of the blood flow index F in the third embodiment.

FIG. 8 is a diagram illustrating a configuration of the biological analysis device 100 according to the third embodiment. The detection device 30A in the biological analysis device 100 according to the third embodiment includes a light-emitting unit E and two light-receiving units R (R1 and R2). As in the second embodiment, the light-emitting unit E radiates a coherent laser light to the measurement region H (biological body) with a narrowband. Each light-receiving unit R receives the laser beam reflected inside the measurement region H as in the second embodiment. The light-receiving units R are each installed at positions located at different distances from the light-emitting unit E. The positions at which the light-receiving units R are installed in the detection device 30A will be described in detail below. Specifically, the light-receiving unit R1 generates a detection signal ZA1 in accordance with a light reception level of the light passing through the inside of the measurement region H and the light-receiving unit R2 generates a detection signal ZA2 in accordance with a light reception level of the light passing through the inside of the measurement region H. The detection signal ZA1 is used in the calculation of the blood flow index F. On the other hand, the detection signal ZA2 is used in the calculation of the absorbance index J.

The index calculation unit 51 according to the third embodiment calculates the blood flow index F from the detection signal ZA1 generated by the light-receiving unit R1 and calculates the absorbance index J from the detection signal ZA2 generated by the light-receiving unit R2. The blood flow index F and the absorbance index J is calculated in accordance with a method similar to that of the second embodiment. The average blood pressure calculation unit 55 according to the third embodiment calculates the average blood pressure Pave from the absorbance index J and the blood flow index F calculated by the index calculation unit 51 as in the second embodiment.

Hereinafter, the positions at which the light-receiving units R are installed in the detection device 30A will be described. Here, a frequency bandwidth (a frequency fL to fH in Expression (5b)) used in the calculation of the blood flow index F in the detection signal Z is different from a frequency bandwidth used in the calculation of the absorbance index J. A distance between the light-emitting unit E to the light-receiving unit R1 (for example, a distance between the centers of the light-emitting unit E and the light-receiving unit R1) in which the detection signal ZA1 with a high SN ratio can be obtained at a frequency bandwidth preferred in the calculation of the blood flow index F is different from a distance between the light-emitting unit E to the light-receiving unit R2 (for example, a distance between the centers of the light-emitting unit E and the light-receiving unit R2) in which the detection signal ZA2 with a high SN ratio can be obtained at a frequency bandwidth preferred in the calculation of the absorbance index J.

FIG. 9 is a table illustrating quality of an SN ratio in a frequency bandwidth used in calculation of the blood flow index F in the detection signal ZA1 and quality of an SN ratio in a frequency bandwidth used in calculation of the absorbance index J in the detection signal ZA2 in a plurality of cases in which a distance between the light-emitting unit E and the light-receiving unit R is changed. As ascertained from FIG. 9, the SN ratio of the frequency bandwidth used in the calculation of the blood flow index F in the detection signal ZA1 indicates a highest value when the distance between the light-emitting unit E and the light-receiving unit R1 is equal to or greater than 0.5 mm and equal to or less than 2 mm. On the other hand, it was possible to obtain the knowledge that the SN ratio of the frequency bandwidth used in the calculation of the absorbance index J in the detection signal ZA2 is a highest value when the distance between the light-emitting unit E and the light-receiving unit R2 is equal to or greater than 3 mm and equal to or less than 5 mm.

On the basis of the foregoing knowledge, according to the third embodiment, distances between the light-emitting unit E and the light reception units R1 and R2 are set separately. For example, the distance between the light-receiving unit R1 and the light-emitting unit E is set as a distance in which the detection signal ZA1 with a high SN ratio can be obtained at a frequency bandwidth preferred in the calculation of the blood flow index F, and the distance between the light-receiving unit R2 and the light-emitting unit E is set as a distance in which the detection signal ZA2 with a high SN ratio can be obtained at a frequency band preferred in the calculation of the absorbance index J. Specifically, on the basis of the result illustrated in FIG. 9, the distance between the light-emitting unit E and the light-receiving unit R1 is set to be equal to or greater than 0.5 mm and equal to or less than 2 mm, and the distance between the light-emitting unit E and the light-receiving unit R2 is set to be equal to or greater than 3 mm and equal to or less than 5 mm (preferably, 4 mm).

In the third embodiment, advantages similar to those of the second embodiment are obtained. In the third embodiment, in particular, since the light-receiving unit R1 calculating the blood flow index F is separate from the light-receiving unit R2 calculating the absorbance index J, it is possible to generate the detection signal ZA1 with the high SN ratio at the frequency band preferred in the calculation of the blood flow index F and the detection signal ZA2 with a high SN ratio at the frequency band preferred in the calculation the absorbance index J. Accordingly, the average blood pressure Pave can be calculated with higher precision than in the configuration in which the light-receiving unit R common to the calculation of the absorbance index J and the calculation of the blood flow index F is used.

Fourth Embodiment

Figure 10:
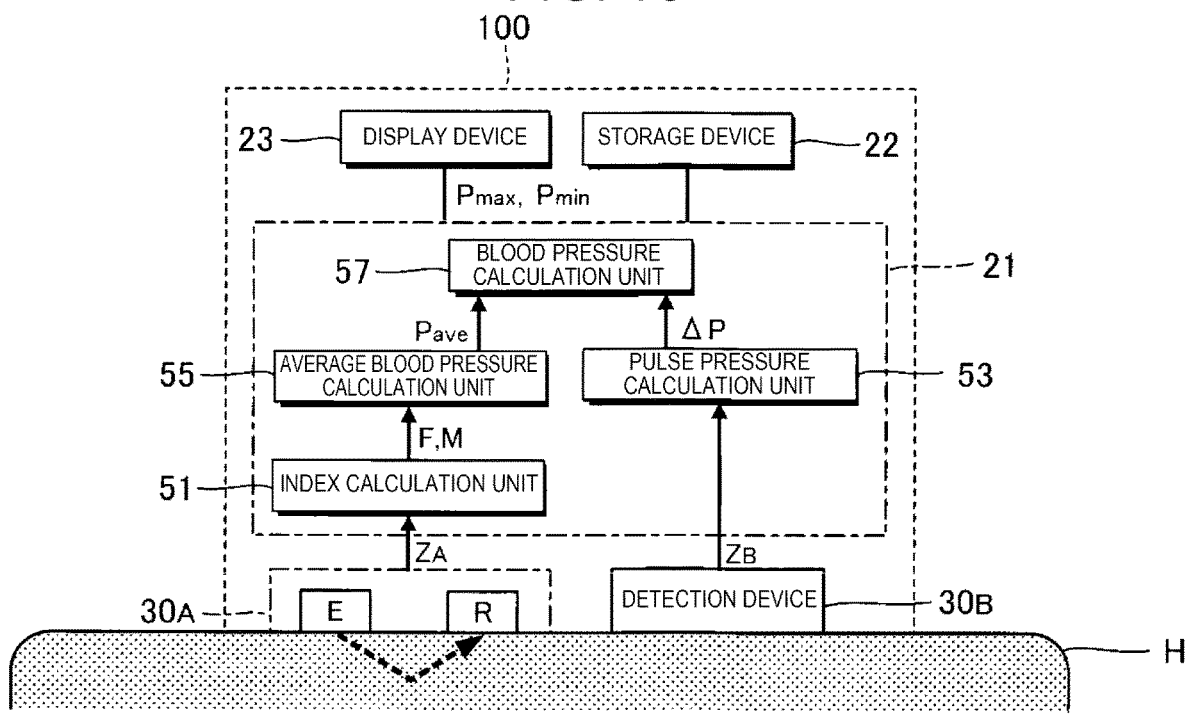
FIG. 10 is a diagram illustrating a configuration of a biological analysis device according to a fourth embodiment.

In a fourth embodiment, a configuration in which a blood pressure P is calculated using the average blood pressure Pave calculated in the first embodiment will be exemplified. FIG. 10 is a diagram illustrating a configuration of a biological analysis device 100 according to the fourth embodiment. The biological analysis device 100 according to the fourth embodiment has a configuration in which a detection device 30B, a pulse pressure calculation unit 53, a blood pressure calculation unit 57 are added to the biological analysis device 100 according to the first embodiment. The pulse pressure calculation unit 53 and the blood pressure calculation unit 57 are realized when the control device 21 executes a program stored in the storage device 22.

The detection device 30B is a detection device that generates a detection signal ZB in accordance with a state of the measurement region H (specifically, a blood vessel inside the measurement region H). For example, a device such as an optical sensor module or an ultrasonic sensor module is appropriately used as the detection device 30B. The pulse pressure calculation unit 53 calculates a pulse pressure ΔP from the detection signal ZB generated by the detection device 30B. The pulse pressure ΔP during the analysis period T exemplified in FIG. 2 is calculated. In the calculation of the pulse pressure ΔP, any known technology can be adopted. The average blood pressure calculation unit 55 calculates the average blood pressure Pave as in the first embodiment.

The blood pressure calculation unit 57 in FIG. 10 calculates the blood pressure P from the pulse pressure ΔP calculated by the pulse pressure calculation unit 53 and the average blood pressure Pave calculated by the average blood pressure calculation unit 55. The blood pressure calculation unit 57 according to the fourth embodiment calculates a systolic blood pressure Pmax and a diastolic blood pressure Pmin. As exemplified in FIG. 2, the systolic blood pressure Pmax is a maximum blood pressure during the analysis period T and the diastolic blood pressure Pmin is a minimum blood pressure during the analysis period T. Relations of Expressions (12) and (13) below are approximately established among the average blood pressure Pave, the pulse pressure ΔP, the systolic blood pressure Pmax, and the diastolic blood pressure Pmin. The blood pressure calculation unit 57 calculates the systolic blood pressure Pmax by Expression (12) below and calculates the diastolic blood pressure Pmin by Expression (13) below. The control device 21 causes the display device 23 to display the systolic blood pressure Pmax and a diastolic blood pressure Pmin calculated by the blood pressure calculation unit 57.

$$P_{max} = P_{ave} + \frac{2}{3}\Delta P \quad (12)$$

$$P_{min} = P_{ave} - \frac{1}{3}\Delta P \quad (13)$$

In the fourth embodiment, advantages similar to those of the first embodiment are obtained. In the fourth embodiment, in particular, since the blood pressures P (the systolic blood pressure Pmax and a diastolic blood pressure Pmin) are calculated from the pulse pressure ΔP and the average blood pressure Pave, an error caused due to a difference in a pressure force can be reduced and the blood pressure P can be calculated with high precision.

Fifth Embodiment

Figure 11:
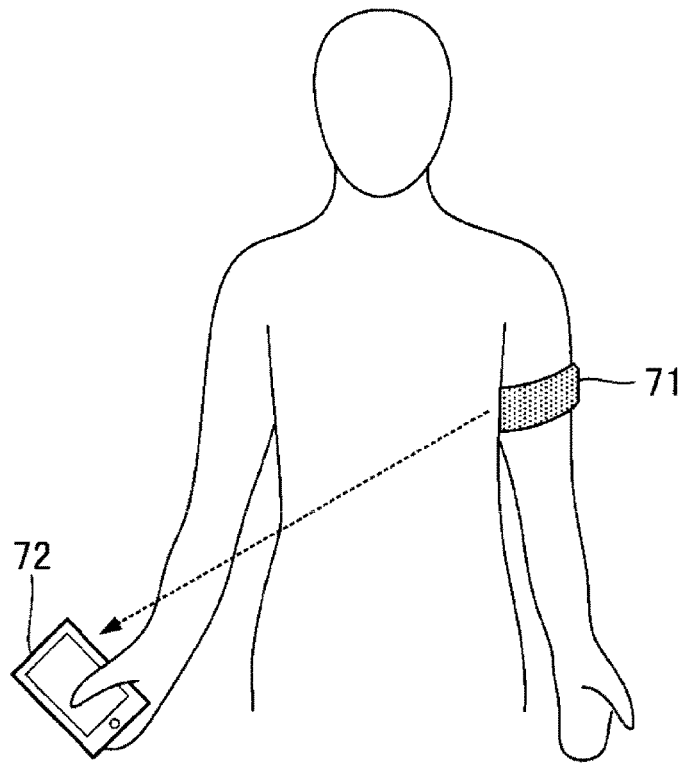
FIG. 11 is a schematic diagram illustrating a use example of a biological analysis device according to a fifth embodiment.
Figure 12:
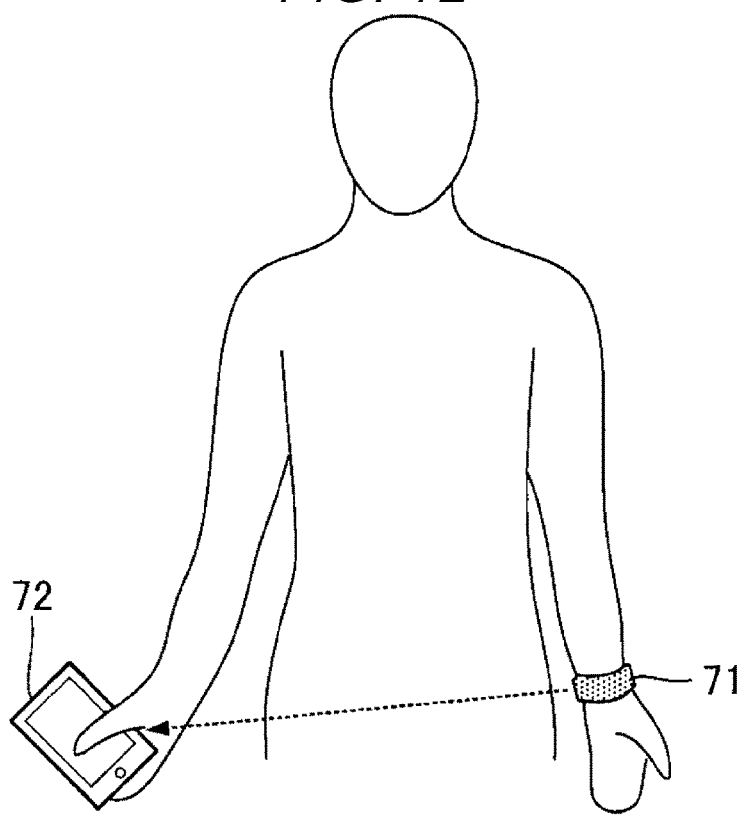
FIG. 12 is a schematic diagram illustrating another use example of the biological analysis device according to the fifth embodiment.

FIG. 11 is a schematic diagram illustrating a use example of a biological analysis device 100 according to a fifth embodiment. As exemplified in FIG. 11, the biological analysis device 100 includes a detection unit 71 and a display unit 72 configured to be separate from each other. The detection unit 71 includes the detection device 30 exemplified in each of the above-described embodiments. FIG. 11 exemplifies the detection unit 71 worn on an upper arm of a subject. As exemplified in FIG. 12, the detection unit 71 worn on a wrist of the subject is also appropriate.

The display unit 72 includes the display device 23 exemplified in each of the above-described embodiments. For example, an information terminal such as a mobile phone or a smartphone is an appropriate example of the display unit 72. Here, any specific form of the display unit 72 is used. For example, a wrist watch type information terminal which can be carried by the subject or an information terminal dedicated for the biological analysis device 100 may be used as the display unit 72.

An element (hereinafter referred to as a "calculation processing unit") calculating the average blood pressure Pave from the detection signal ZA is mounted on, for example, the display unit 72. The calculation processing unit includes the elements exemplified in FIG. 3 (the index calculation unit 51 and the average blood pressure calculation unit 55). The detection signal ZA generated by the detection device 30 of the detection unit 71 is transmitted to the display unit 72 in a wired or wireless manner. The calculation processing unit of the display unit 72 calculates the average blood pressure Pave from the detection signal ZA and displays the average blood pressure Pave on the display device 23. The pulse pressure calculation unit 53 and the blood pressure calculation unit 57 exemplified in the fourth embodiment can also be mounted on the display unit 72.

The calculation processing unit may be mounted on the detection unit 71. The calculation processing unit calculates the average blood pressure Pave from the detection signal ZA generated by the detection device 30 and transmits data for displaying the average blood pressure Pave to the display unit 72 in a wired or wireless manner. The display device 23 of the display unit 72 displays the average blood pressure Pave indicated by the data received from the detection unit 71. The calculation processing unit may transmit data for displaying the blood pressure calculated in the fourth embodiment to the display unit 72.

Sixth Embodiment

Figure 13:
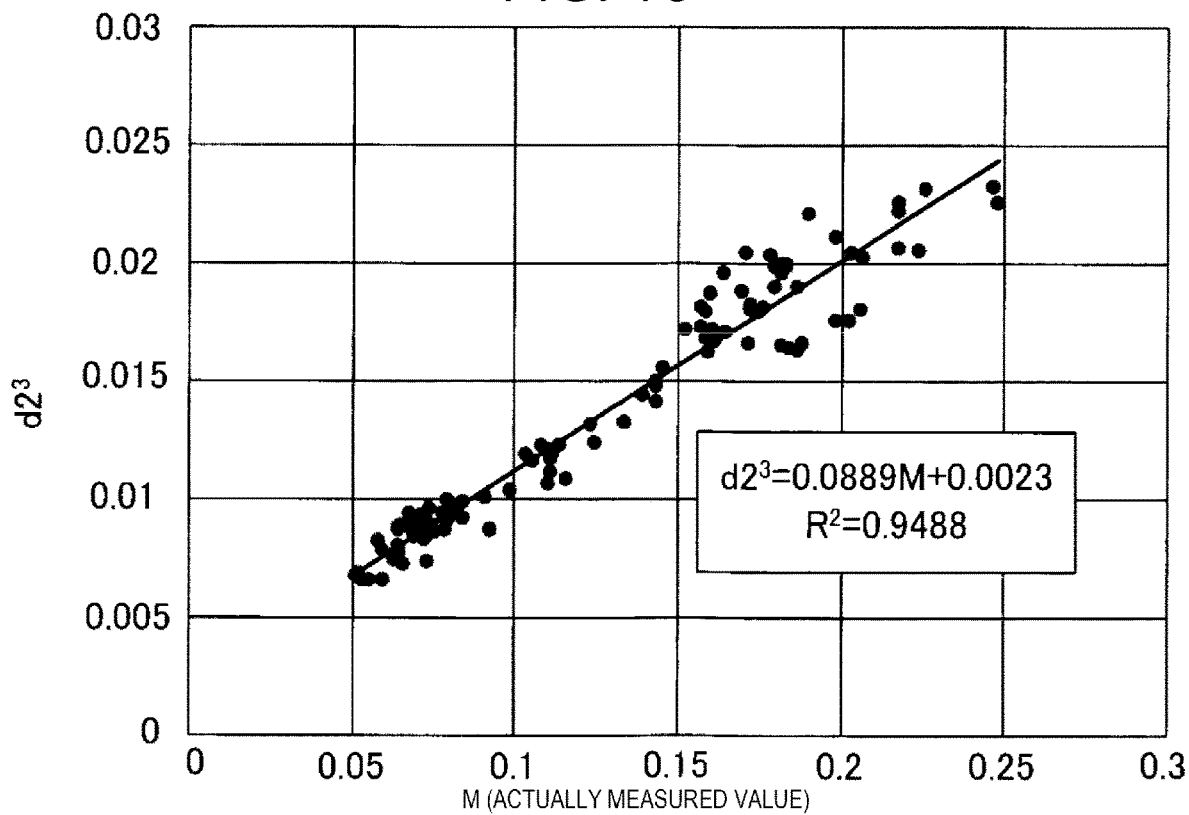
FIG. 13 is a graph illustrating a relation between an actually measured value of a blood mass index and a cubic power of a blood vessel diameter according to a sixth embodiment.

FIG. 13 is a graph illustrating a relation between actually measured values of the blood mass index M and a third power ($d2^3$) of the blood vessel diameter d2 calculated from the actually measured values of the blood flow index F and the actually measured values of the average blood pressure Pave. The actually measured value of the blood mass index M and the actually measured value of the blood flow index F are measured using, for example, a laser Doppler blood flowmeter. The average blood pressure Pave is measured using a cuff or the like. FIG. 13 illustrates a result measured on a plurality of subjects. As described above, the blood vessel diameter d2 is equivalent to a cubic root ($M^{1/3}$) of the blood mass index M. Therefore, Expression (7) below is derived from Expression (14). $d2^3$ is calculated using Expression (14).

$$d2^3 = K\left(\frac{F_{ave}}{P_{ave}}\right)^{\frac{3}{4}} \quad (14)$$

As ascertained form FIG. 13, it is possible to obtain the knowledge that a regression line indicating a relation between $d2^3$ and the actually measured value of the blood mass index M is expressed by a linear function that has a slope and an intercept. When a is a coefficient indicating the slope and b is a coefficient indicating the intercept, $d2^3$ is expressed in Expression (15) below. FIG. 13 exemplifies a case in which the coefficient a is 0.0889 and the coefficient b is 0.0023. The actually measured value of blood mass index M and $d2^3$ have high correlation, it can be understood that the correlation is appropriately approximate by Expression (15) A correlation coefficient $R^2$ in FIG. 13 is 0.9488.

$$d2^3 = a \times M + b \quad (15)$$

On the premise that the third power of the blood vessel diameter d2 is equivalent to the blood mass index M and the flood flow index F is equivalent to the blood flow Q2, Expression (4) described above is modified to Expression (16) below. A sign K' in Expression (16) is a coefficient determined in advance in accordance with the blood density ρ, a length L2 of an arteriole, and the like as in the coefficient K in Expression (7).

$$P_{ave} = K' \times \frac{F}{(a \times M + b)^{\frac{4}{3}}} \quad (16)$$

Figure 14:
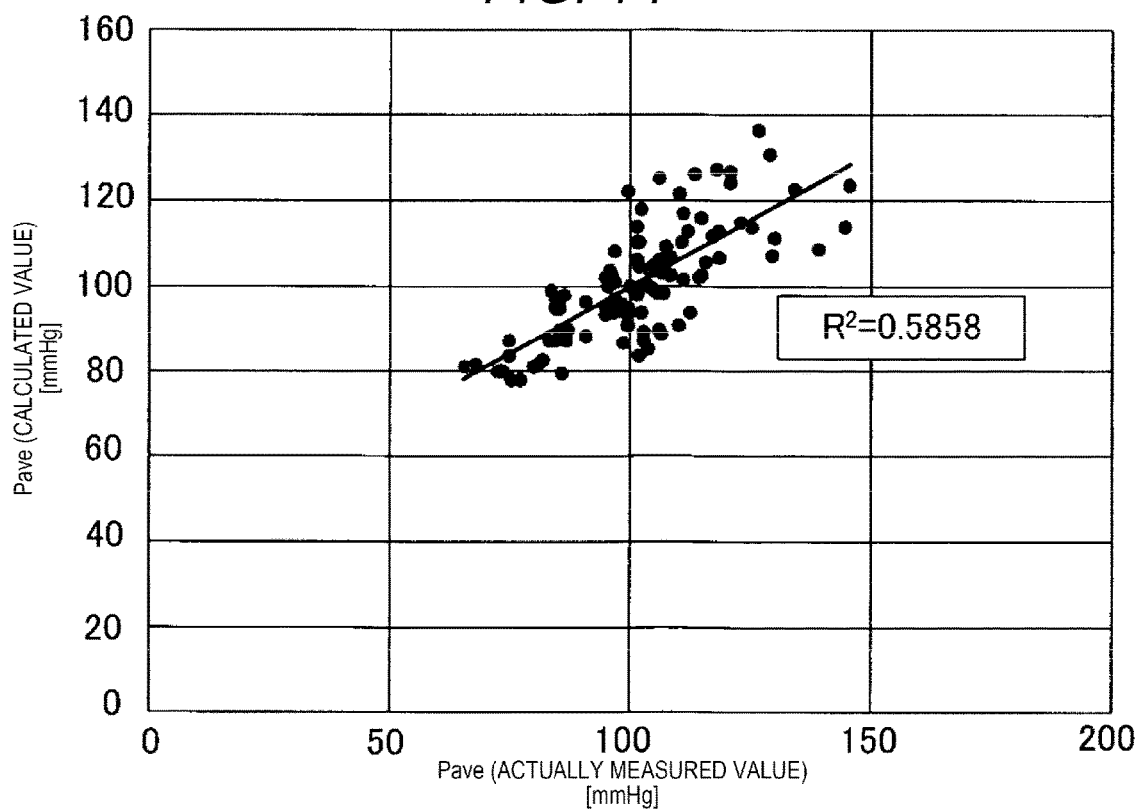
FIG. 14 is a graph illustrating a relation between average blood pressures and average blood pressures (calculated values) according to the sixth embodiment.

FIG. 14 is a graph illustrating a relation between actually measured values of the average blood pressure Pave measured by a cuff or the like and the calculated values of the average blood pressure Pave calculated from Expression (16) Negative correlation is observed between the actually measured value of the average blood pressure Pave and a calculated value of the average blood pressure Pave observed on the assumption that $d2^3$ has no intercept in some cases. In contrast, as ascertained in FIG. 14, positive correlation was observed between the actually measured value of the average blood pressure Pave and the calculated value of the average blood pressure Pave calculated by Expression (16). The correlation coefficient $R^2$ in FIG. 34 is 0.5858. On the basis of the foregoing knowledge, the average blood pressure Pave is calculated using Expression (16) in the sixth embodiment. That is, the average blood pressure Pave is calculated by $F_{ave}/(a \times M_{ave} + b)^{4/3}$.

The coefficients a and b in Expression (16) are statistically set, for example, using the actually measured values (the average blood pressure Pave, the blood mass index M, and the blood flow index F) calculated from a plurality of subjects. The coefficients a and b may be set for each user of the biological analysis device 100 or the coefficients a and b common to users may be set. When the coefficients a and b are set for each user, it is necessary to correct the coefficients a and b using actually measured values measured for each user. On the other hand, when the coefficients a and b common to users are set, there is the advantage that correction is not necessary for each user. One of the coefficients a and b may be set to be common to the users and the other may be set for each user.

As understood from the foregoing description, according to the sixth embodiment, the average blood pressure Pave is calculated in accordance with $F_{ave}/(a \times M_{ave} + b)^{4/3}$ which is observed to have positive correlation with the actually measured value of the average blood pressure Pave. Therefore, it is possible to calculate the average blood pressure Pave with high precision. When the coefficients a and b are set to be common to the users, there is the advantage that the correction is not necessary at the time of using the biological analysis device 100. The configuration of the sixth embodiment can be applied to any of the first to fifth embodiments.

Seventh Embodiment

Noise distributed with a substantially equal intensity in a whole region on the frequency axis (hereinafter referred to as "background noise") can be contained in the intensity spectrum related to a frequency of the detection signal ZA. The background noise is shot noise unique to an electric circuit included in the biological analysis device 100 or noise caused due to an electromagnetic wave in an installation environment of the biological analysis device 100. In a seventh embodiment, the background noise is reduced from an intensity spectrum specified from the detection signal ZA, and the blood mass index M and the blood flow index F are calculated.

The detection device 30A according to the seventh embodiment generates a signal indicating the background noise (hereinafter referred to as an "observation signal") in addition to the detection signal ZA exemplified in each of the above-described embodiments. The observation signal is generated in a state in which a blood flow is not observed. For example, a signal output by the light-receiving unit R is generated as an observation signal in a state in which the light-emitting unit E radiates light to a stationary object with low reflectance without including a moving object. A signal output by the light-receiving unit R may be used as an observation signal in a state in which light is not radiated to a stationary object. A signal output by the light-receiving unit R may be used as an observation signal in a state in which the measurement region H or a position upstream from the measurement region H is stopped from bleeding by a cuff or the like. As understood from the foregoing description, an observation signal containing no component originating from a blood flow of the measurement region H is generated. That is, an observation signal indicating the background noise in a case in which the blood mass index M and the blood flow index F of the measurement region H are calculated is generated.

The index calculation unit 51 according to the seventh embodiment subtracts an intensity G(f)bg of the background noise from an intensity G(f) at each frequency f in an intensity spectrum related to the frequency of the detection signal ZA and calculates the blood mass index M and the blood flow index F. The intensity G(f)bg of the background noise is an intensity at each frequency f in the intensity spectrum calculated from the observation signal. A value obtained by smoothing the intensity G(f)bg of the background noise (for example, moving average) may be subtracted from the intensity G(f). The intensity G(f)bg may be smoothed on either the time axis or the frequency axis.

Specifically, the index calculation unit 51 specifies a correction intensity G(f)c by subtracting the intensity G(f)bg from the intensity G(f) at each frequency f. The correction intensity G(f)c is expressed in Expression (17) below.

$$G(f)c = G(f) - G(f)bg \tag{17}$$

The blood mass index M and the blood flow index F are calculated using the correction intensity G(f)c calculated from Expression (17). That is, the blood mass index M and the blood flow index F from which an influence of the background noise is reduced are calculated. As in each of the above-described embodiments, Expression (5a) or (5b) is used in the calculation of the blood mass index M, and Expression (6a) or (6b) is used in the calculation of the blood flow index F.

As understood from the foregoing description, according to the seventh embodiment, the intensity G(f)bg of the background noise is subtracted from the intensity G(f) at each frequency f in the intensity spectrum of the detection signal ZA to calculate the blood mass index M and the blood flow index F. Accordingly, the blood mass index M and the blood flow index F from which an influence of the background noise is reduced are calculated. That is, it is possible to calculate the average blood pressure Pave with high precision.

As ascertained from Expression (6a) or (6b), the blood flow index F is calculated by multiplying the intensity G(f) by the frequency f (that is, using a frequency weighted intensity spectrum (f×G(f))). Accordingly, there is a tendency that the influence of the background noise increases with respect to the blood flow index F as the frequency f increases. The configuration in which the background noise is reduced from the intensity spectrum according to the seventh embodiment is particularly effective when the blood flow index F is calculated. The configuration of the seventh embodiment can be used to reduce the background noise from the intensity spectrum of the optically detected detection signal in the first to sixth embodiments.

Eighth Embodiment

When the background noise is removed at a frequency bandwidth (hereinafter referred to as a "designation bandwidth") in which the intensity G(f) is not changed in accordance with pulsation of the measurement region H in the intensity spectrum of the detection signal ZA in the seventh embodiment, the intensity G(f) becomes closes to 0. As the intensity G(f) in the designation bandwidth is closer to 0, the background noise is paraphrased as being removed with high precision. Accordingly, in an eighth embodiment, the intensity G(f)bg is subtracted from the intensity G(f) so that a result obtained by subtracting the intensity G(f)bg from the intensity G(f) is closer to 0 in the designation bandwidth. The designation bandwidth is, for example, a bandwidth equal to or greater than 25 kHz or equal to or less than 30 kHz. The designation bandwidth is not limited to the foregoing example. For example, the designation bandwidth is changed appropriately in accordance with the kind of measurement region H.

The index calculation unit 51 according to the eighth embodiment calculates the blood mass index M and the blood flow index F by subtracting the intensity G(f)bg of the background noise from the intensity G(f) at each frequency f in the intensity spectrum related to the frequency of the detection signal ZA as in the seventh embodiment. Specifically, the index calculation unit 51 calculates the correction intensity G(f)c by subtracting the intensity G(f)bg from the intensity G(f) so that the result obtained by subtracting the intensity G(f)bg from the intensity G(f) is close to 0 in the designation bandwidth. The correction intensity G(f)c according to the eighth embodiment is expressed in Expression (18) below.

$$G(f)c = G(f) - C \times G(f)bg \tag{18}$$

A sign C in Expression (18) is a coefficient set so that the correction intensity G(f)c in the designation bandwidth is closer to 0. Specifically, the coefficient C is set so that a value calculated from Expression (19) below is minimum (ideally, 0). A sign fmax of Expression (18) is an upper limit of the frequency of the designation bandwidth and fmin is a lower limit of the frequency of the designation bandwidth. The coefficient C may be set in accordance with the frequency f. For example, the coefficient C different for each bandwidth segmented into a plurality of pieces on the frequency axis may be set.

$$\sum_{fmin}^{fmax} (G(f) - C \times G(f)bg)^2 \tag{19}$$

As ascertained from Expression (18), the correction intensity G(f)c is calculated by subtracting the intensity G(f)bg multiplied by the coefficient C from the intensity G(f). The index calculation unit 51 calculates the blood mass index M and the blood flow index F using the correction intensity G(f)c calculated by Expression (18) at each frequency f. As in each of the above-described embodiments, Expression (5a) or (5b) is used in the calculation of the blood mass index M, and Expression (6a) or (6b) is used in the calculation of the blood flow index F.

Figure 15:
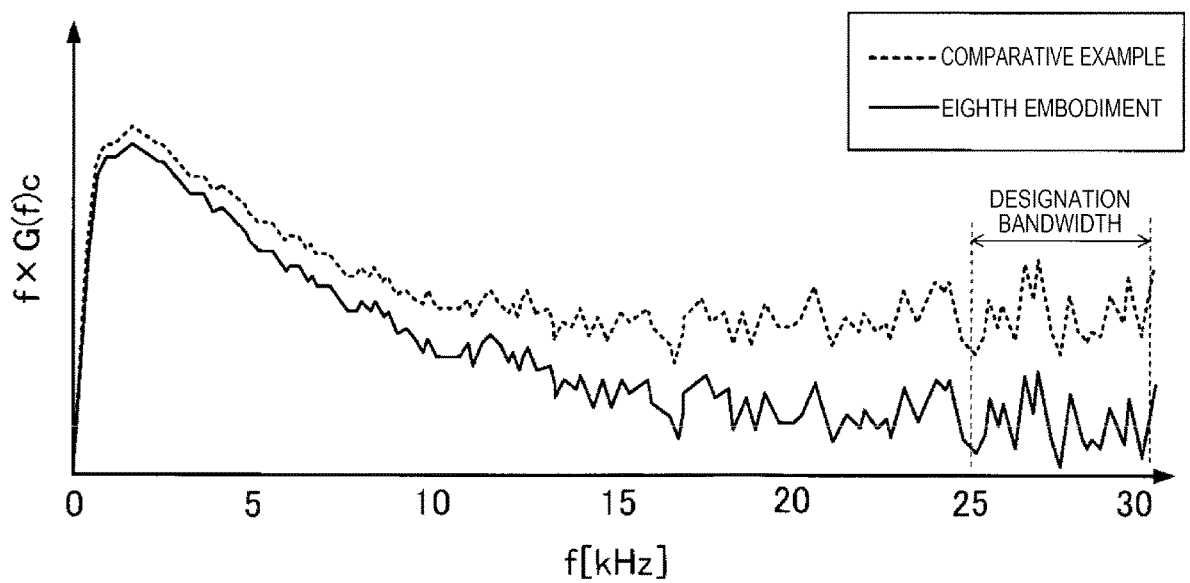
FIG. 15 is a graph illustrating a frequency weighted intensity spectrum according to an eighth embodiment and a comparative example.

FIG. 15 is graph illustrating the frequency weighted intensity spectrum (f×G(f)c) calculated in a configuration in which the correction intensity G(f)c is calculated without multiplying the intensity G(f)b by the coefficient C (hereinafter referred to as a "comparative example") and the frequency weighted intensity spectrum (f×G(f)c) calculated from the correction intensity G(f)c by calculating Expression (18). As ascertained from FIG. 15, in the configuration of the eighth embodiment, the frequency weighted intensity spectrum (f×G(f)c) is calculated by reducing the background noise with higher precision than in the comparative example. In particular, the background noise is effectively reduced on a high bandwidth in which an influence of the background noise increases and the frequency weighted intensity spectrum (f×G(f)c) is calculated. That is, it is possible to calculate the blood flow index F from which the background noise is effectively reduced over the whole frequency axis.

Figure 16:
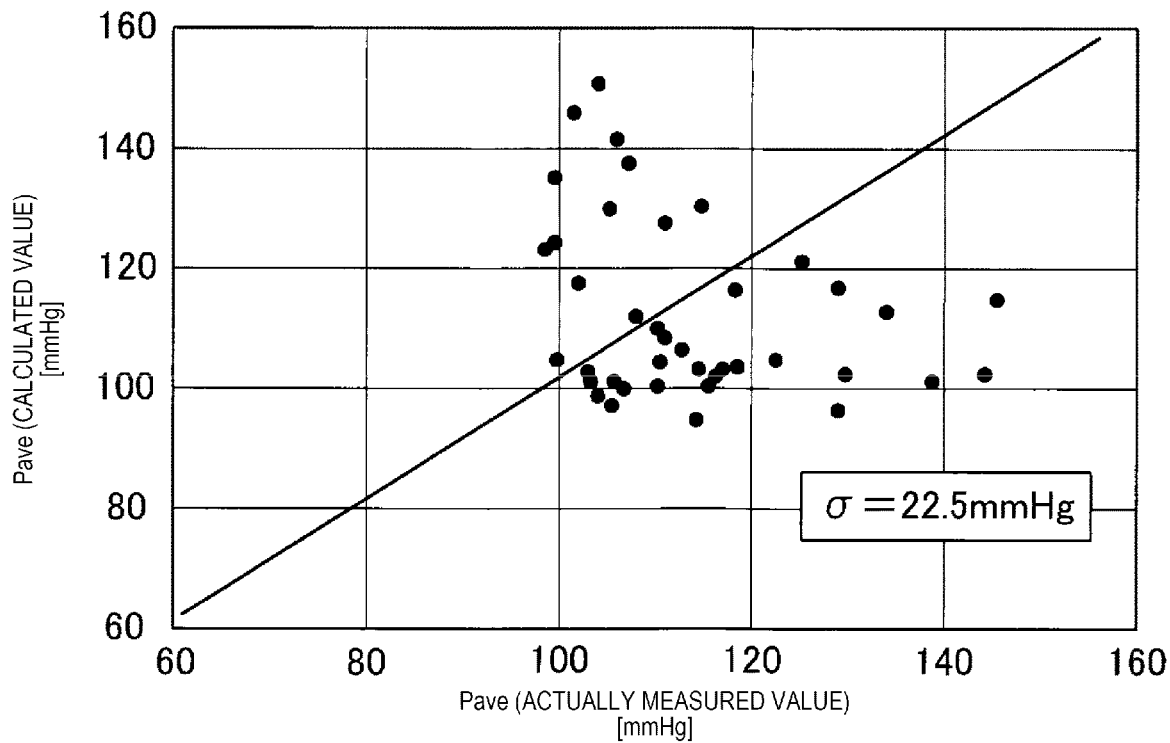
FIG. 16 is a graph illustrating a relation between an average blood pressure (calculated value) in the comparative example and an average blood pressure (actually measured value).
Figure 17:
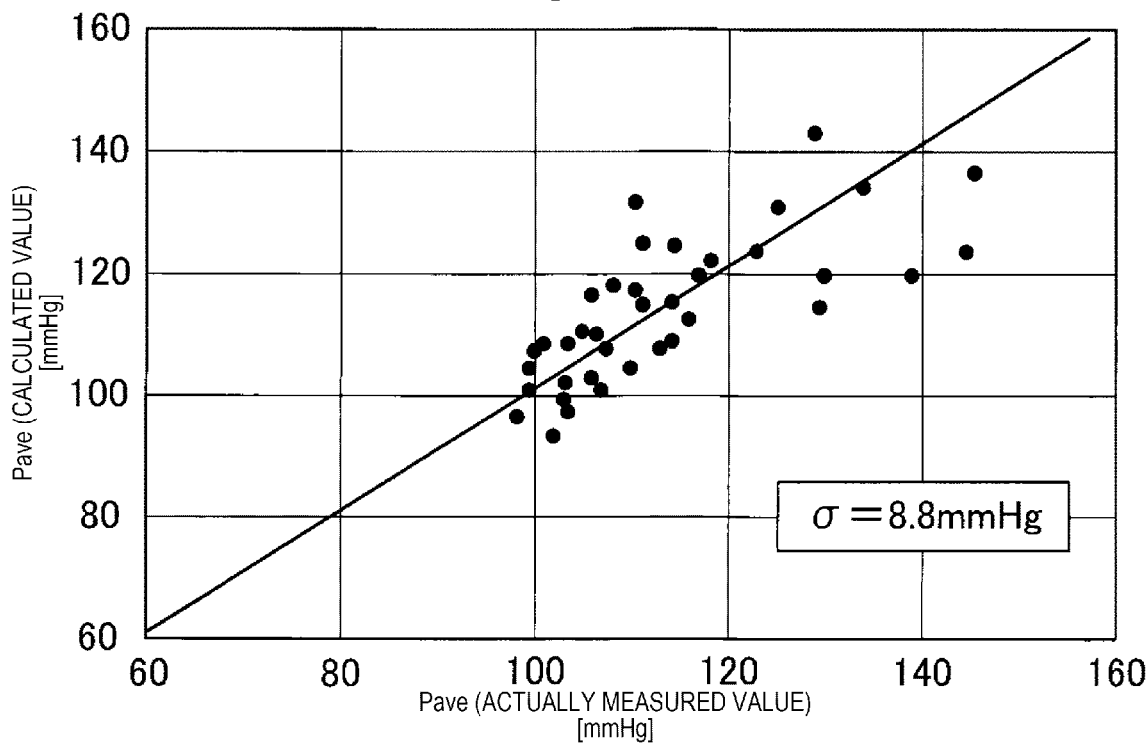
FIG. 17 is a graph illustrating a relation between an average blood pressure (calculated value) and an average blood pressure (actually measured value) according to the eighth embodiment.

FIG. 16 is a graph illustrating a relation between a calculated value of the average blood pressure Pave calculated in the comparative example and actually measured value of the average blood pressure Pave measured by a cuff or the like. FIG. 17 is a graph illustrating a relation between a calculated value of the average blood pressure Pave calculated in the configuration of the eighth embodiment and an actually measured value of the average blood pressure Pave measured by a cuff or the like. As ascertained from FIGS. 16 and 17, according to the eighth embodiment, higher correlation (positive correlation) is observed between the calculated value of the average blood pressure Pave and the actually measured value of the average blood pressure Pave than in the comparative example. While a standard deviation σ of the calculated values of the average blood pressure Pave in FIG. 16 is 22.5 mmHg, the standard deviation σ of the calculated values of the average blood pressure Pave in FIG. 17 is 8.8 mmHg. As described above, according to the eighth embodiment, it can be understood that the average blood pressure Pave can be calculated with higher precision than in the comparative example.

In the eighth embodiment, advantages similar to those of the first embodiment are obtained. In the eighth embodiment, the blood mass index M and the blood flow index F in which the influence of the background noise is reduced are calculated as in the seventh embodiment. According to the eighth embodiment, in particular, the blood mass index M and the blood flow index F are calculated by subtracting the intensity G(f)bg from the intensity G(f) so that the result obtained by subtracting the intensity G(f)bg from the intensity G(f) is closer to 0 in the designation bandwidth. Accordingly, it is possible to reduce the influence of the background noise with higher precision and calculate the blood mass index M and the blood flow index F than in the comparative example.

Examination on Presence or Absence of Each Configuration

As has been exemplified in each of the above-described embodiments, according to a preferred aspect of the invention, a configuration in which the average blood pressure Pave is calculated in accordance with the blood vessel diameter index and the blood flow index F (hereinafter referred to as a "configuration A") is adopted. A method of determining whether the configuration A is adopted in an actual biological analysis device (hereinafter referred to as an "actual product") 90 will be described below. Hereinafter, the biological analysis device 100 for which it is confirmed that the configuration A is adopted is referred to as a "product of the present specification".

Figure 18:
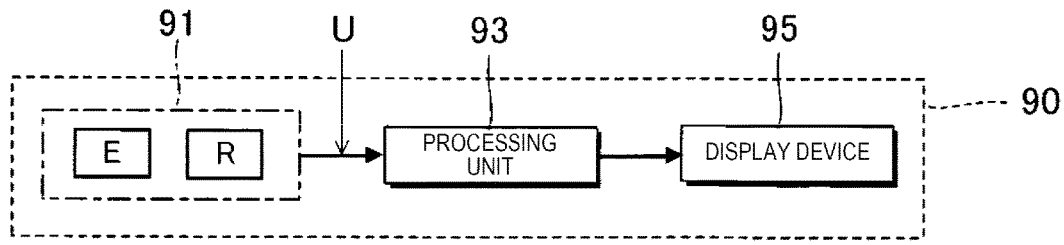
FIG. 18 is a diagram illustrating a configuration of an actual product.

The actual product 90 includes a detection device 91 that includes the light-emitting unit E and the light-receiving unit R, a processing unit 93 that calculates an average blood pressure PWave from a detection signal output by the detection device 91, and a display device 95 that displays the average blood pressure PWave calculated by the processing unit 93, as exemplified din FIG. 18. A scene in which a plurality (for example, 3 or more kinds) of test signals U with different waveforms within the analysis period T are supplied in order to each of the processing unit 93 of the actual product 90 and the control device 21 of the product of the present specification is assumed. In the actual product 90, each test signal U (U1, U2, and U3) is supplied to the processing unit 93 (for example, a wiring or a terminal between the detection device 91 and the processing unit 93). For example, each test signal U is generated by a signal generator such as a pulse generator. The plurality of test signals U have different Fave/Mave$^{4/3}$ (Fave/Jave$^4$ in the product of the present specification in the second and third embodiments). For example, the plurality of test signals U are generated so that a difference between a maximum value and a minimum value among Fave/Mave$^{4/3}$ calculated in the plurality of test signals U is twice or more. The test signals U with wavelengths of a time length longer than the analysis period T may be generated.

A case in which the average blood pressure Pave of a subject is displayed as a measurement result on the display device 95 of the actual product 90 is assumed. It is assumed that an average blood pressure PWave1 is displayed when the test signal U1 is supplied to the actual product 90, an average blood pressure PWave2 is displayed when the test signal U2 is supplied to the actual product 90, and an average blood pressure PWave3 is displayed when the test signal U3 is supplied to the actual product 90. It is assumed that the average blood pressure Pave1 is displayed when the test signal U1 is supplied to the product of the present specification, the average blood pressure Pave2 is displayed when the test signal U2 is supplied to the product of the present specification, and the average blood pressure Pave3 is displayed when the test signal U3 is supplied to the product of the present specification.

Figure 19:
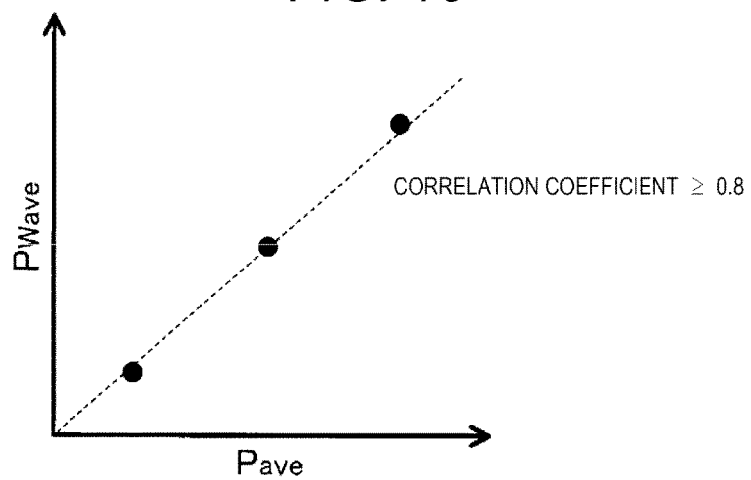
FIG. 19 is a graph illustrating a relation between an average pulse pressure displayed for an actual product and an average pulse pressure displayed for a product of the present specification.

FIG. 19 is a graph illustrating a relation between the average blood pressure PWave displayed on the actual product 90 and the average blood pressure Pave displayed on the product of the present specification. When the configuration A is adopted in the actual product 90, correlation is observed between the plurality of average blood pressures PWave (the average blood pressures PWave1, PWave2, and PWave3) measured with the actual product 90 and the plurality of average blood pressures Pave (Pave1, Pave2, and Pave3) measured with the product of the present specification. Specifically, a correlation coefficient between the plurality of average blood pressures PWave displayed on the actual product 90 and the plurality of average blood pressures Pave displayed with the product of the present specification is 0.8 or more. In consideration of the foregoing circumstances, there is a sufficiently high possibility of the configuration A being adopted in the actual product 90 when the correlation coefficient between the average blood pressures Pave calculated by supplying the plurality of test signals U to the actual product 90 and the average blood pressure Pave calculated by supplying the plurality of test signals U to the product of the present specification is 0.8 or more. For example, a Pearson integration correlation coefficient is suitable as the correlation coefficient.

In the foregoing description, the test signals U have been supplied to the processing unit 93 of the actual product 90, but the average pulse pressures PWave calculated by causing the light-receiving unit R that generates a detection signal in the actual product 90 to receive light by which the test signals U are generated may be compared with the average pulse pressures Pave of the product of the present specification. In the foregoing description, the average pulse pressures PWave displayed on the display device 95 of the actual product 90 have been compared with the average pulse pressures Pave displayed on the display device 23 of the product of the present specification, but whether the actual product 90 has the configuration A may be determined by comparing data output from the processing unit 93 of the actual product 90 with data output from the control device 21 of the product of the present specification.

In the foregoing description, the case in which the actual product 90 displays the average pulse pressures PWave has been assumed for convenience, but whether the actual product 90 has the configuration A can be estimated in accordance with a similar method even when the actual product 90 displays the blood pressures P (Pmax and Pmin) of a subject. That is, a correlation coefficient is calculated between the plurality of blood pressures measured by sequentially supplying the plurality of test signals U to the actual product 90 and the plurality of blood pressures measured by sequentially supplying the plurality of test signals U to the product of the present specification (in the fourth embodiment) When the correlation coefficient is 0.8 or more, there is a high possibility of the configuration A being adopted in the actual product 90.

In the seventh and eighth embodiments, a configuration in which the blood vessel diameter index and the blood flow index F are calculated by subtracting the intensity G(f)bg of the background noise from the intensity G(f) at each frequency f in the intensity spectrum related to the frequency of the detection signal ZA (hereinafter referred to as a "configuration B") is adopted. A method of determining whether the configuration B is adopted in the actual product 90 will be described below.

In a state in which the measurement region H or a position upstream from the measurement region H is stopped from bleeding (hereinafter referred to as a "bleeding stop state"), the average pulse pressure PWave is calculated by the actual product 90. In the intensity spectrum specified by the actual product 90 in the bleeding stop state, the background noise is predominantly contained. When the configuration B is adopted in the actual product 90, the average pulse pressure PWave is a value close to 0 (ideally, 0) in the bleeding stop state. On the other hand, when the configuration B is not adopted in the actual product 90, the average pulse pressure PWave is a value deviating from 0 due to an influence of the background noise contained in the intensity spectrum. As understood from the foregoing description, there is a high possibility of the configuration B being adopted when the average pulse pressure PWave displayed on the actual product 90 is close to 0 in the bleeding stop state. When the actual product 90 displays the blood vessel diameter index or the blood flow index F, whether the configuration B is adopted may be determined by determining whether the blood vessel diameter index or the blood flow index F calculated in the bleeding stop state is close to 0.

Modification Examples

Each of the embodiments exemplified above can be modified in various forms. Specific modification aspects will be exemplified below. Two or more selected arbitrarily from the following examples can also be merged appropriately.

(1) In each of the above-described embodiments, the average blood pressure Pave has been calculated, but the biological information calculated by the biological analysis device 100 is not limited to the foregoing example. For example, the average blood pressure calculation unit 55 may specify an index (for example, abnormality/high side/normality or the like) indicating a state of the average blood pressure Pave of a subject using the calculated average blood pressure Pave. As understood from the foregoing description, the index calculated by the average blood pressure calculation unit 55 is comprehensively expressed as an index related to the average blood pressure Pave (hereinafter referred to as an "average blood pressure index"), the average blood pressure index includes both the average blood pressure Pave and an index calculated using the average blood pressure Pave.

(2) In each of the above-described embodiments, the average blood pressure Pave has been calculated in accordance with the average value obtained by averaging the blood vessel diameter indexes (the blood mass indexes M or the absorbance indexes J) during the analysis period T and the average value Fave obtained by averaging the blood flow indexes F during the analysis period T, but a method of calculating the average blood pressure Pave is not limited to the foregoing example. A configuration in which a time length of the analysis period T in which the blood vessel diameter indexes are averaged is caused to be different from a time length of the analysis period T in which the blood flow indexes F are averaged or a configuration in which the analysis period T in which the blood vessel diameter indexes are averaged does not overlap the analysis period T in which the blood flow indexes F are averaged on the time axis can be adopted.

In the first embodiment (and the fourth or fifth embodiment), the average value Mave has been calculated by averaging the plurality of blood mass indexes M within the analysis period T and the average value Fave has been calculated by averaging the plurality of blood flow indexes F, but methods of calculating the average value Mave and the average value Fave are not limited to the foregoing example. For example, the average value Mave and the average value Fave may be calculated by calculating the average intensity spectrum by averaging the plurality of intensity spectra calculated at time points different within the analysis period T to calculate the average intensity spectrum and performing the calculation in the average intensity spectrum. The average value Jave in the second and third embodiment can also be similarly calculated from the average intensity spectrum. When the average intensity $<I^2>$ is changed within the analysis period T, there is a possibility of the average blood pressure Pave not being appropriately calculated in the configuration in which the average intensity spectrum is used. Accordingly, even when the average intensity $<I^2>$ is changed, a configuration in which the average value Mave and the average value Fave are calculated at each time point within the analysis period T is appropriate, as exemplified in the above-described first embodiment, from the viewpoint of calculating the average blood pressure Pave with high precision.

(3) In the first embodiment (and the fourth or fifth embodiment), the detection signal ZA generated by the common light-receiving unit R has been used in the calculation of the blood mass index M and the calculation of the blood flow index F, but the detection signals Z generated by the separate light-receiving units R can also be used in the calculation of the blood vessel diameter index and the calculation of the blood flow index F. Specifically, the detection device 30A includes a light-emitting unit E and two light-receiving units R (R1 and R2). An intensity spectrum of the detection signal Z generated by the light-receiving unit R1 is used in the calculation of the blood mass index M and an intensity spectrum of the detection signal Z generated by the light-receiving unit R2 is used in the calculation of the blood flow index F. Here, in the configuration of the first embodiment in which the detection signal ZA generated by the common light-receiving unit R is used in the calculation of the blood mass index M and the calculation of the blood flow index F, an intensity spectrum common to the calculation of the blood mass index M and the calculation of the blood flow index F can be used.

(4) In each of the above-described embodiments, the biological analysis device 100 configured as a single device has been described, but as will be exemplified below, the plurality of components of the biological analysis device 100 can be realized as mutually separate devices. In the following description, an element calculating the average blood pressure Pave from the detection signal Z is referred to as a "calculation processing unit 27". The calculation processing unit 27 includes, for example, the components exemplified in FIG. 5 (the index calculation unit 51 and the average blood pressure calculation unit 55).

Figure 20:
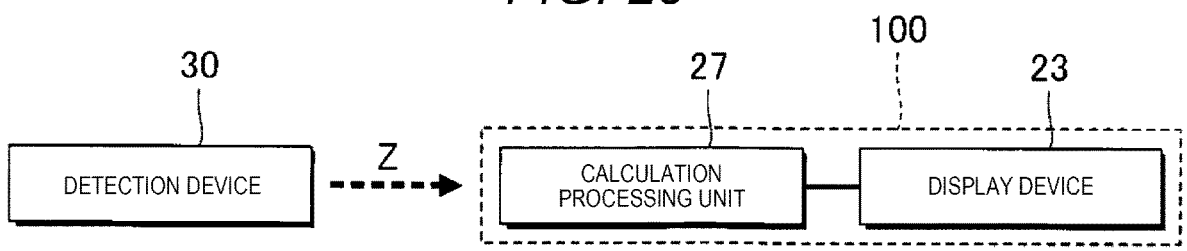
FIG. 20 is a diagram illustrating a configuration of a biological analysis device according to a modification example.

In each of the above-described embodiments, the biological analysis device 100 including the detection devices 30 (30A and 30B) has been exemplified, but as exemplified in FIG. 20, the detection device 30 is assumed to be separate from the biological analysis device 100. The detection device 30 is, for example, a portable optical sensor module that is worn on the measurement region H such as a wrist, an upper wrist, or the like of a subject. The biological analysis device 100 is realized as, for example, an information terminal such as a mobile phone or a smartphone. The biological analysis device 100 may be realized as a wrist watch type information terminal. The detection signal Z generated by the detection device 30 is transmitted to the biological analysis device 100 in a wired or wireless manner. The calculation processing unit 27 of the biological analysis device 100 calculates the average blood pressure Pave from the detection signal Z and displays average blood pressure Pave on the display device 23. As understood from the foregoing description, the detection device 30 can be omitted from the biological analysis device 100.

Figure 21:
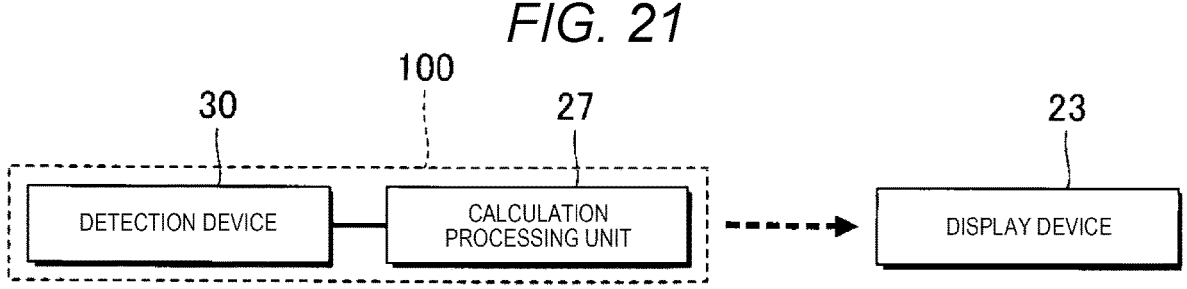
FIG. 21 is a diagram illustrating a configuration of a biological analysis device according to a modification example.

In each of the above-described embodiments, the biological analysis device 100 including the display device 23 has been exemplified, but as exemplified in FIG. 21, the display device 23 may be configured to be separate from the biological analysis device 100. The calculation processing unit 27 of the biological analysis device 100 calculates the average blood pressure Pave from the detection signal Z and transmits data for displaying the average blood pressure Pave to the display device 23. The display device 23 may be a dedicated display device, but may be mounted on, for example, an information terminal such as a mobile phone or a smartphone or a wrist watch type information terminal which can be carried by a subject. The average blood pressure Pave calculated by the calculation processing unit 27 of the biological analysis device 100 are transmitted to the display device 23 in a wired or wireless manner. The display device 23 displays the average blood pressure Pave (the blood pressure in the fourth embodiment) received from the biological analysis device 100. As understood from the foregoing description, the display device 23 can be omitted from the biological analysis device 100.

Figure 22:
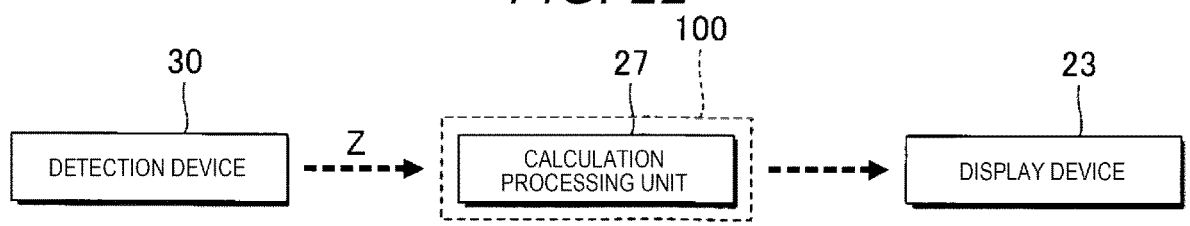
FIG. 22 is a diagram illustrating a configuration of a biological analysis device according to a modification example.

As exemplified in FIG. 22, the detection device 30 and the display device 23 are assumed to be separate from the biological analysis device 100 (the calculation processing unit 27). For example, the biological analysis device 100 (the calculation processing unit 27) is mounted on an information terminal such as a mobile phone or a smartphone.

In the configuration in which the detection device 30 is separate from the biological analysis device 100, the index calculation unit 51 can also be mounted on the detection device 30. The blood vessel diameter index and the blood flow index F calculated by the index calculation unit 51 are transmitted from the detection device 30 to the biological analysis device 100 in a wired or wireless manner. As understood from the foregoing description, the index calculation unit 51 can be omitted from the biological analysis device 100.

(5) In each of the above-described embodiments, the wrist watch type biological analysis device 100 including the casing 12 and the belt 14 has been exemplified, but any specific form of the biological analysis device 100 can be used. For example, the biological analysis device 100 of any type such as a patch type which can be attached to the body of a subject, an ear-mounted type which can be mounted on the ears of a subject, a finger-mounted type (for example, a nail-mounted type) which can be mounted on a finger of a subject), or a head-mounted type which can be mounted on the head of a subject can be adopted.

(6) In each of the above-described embodiments, the average blood pressure Pave (the blood pressure P in the fourth embodiment) of a subject has been displayed on the display device 23, but the configuration in which the subject is informed of the average blood pressure Pave is not limited to the foregoing example. For example, a subject can also be informed of the average blood pressure Pave by sound. In the ear-mounted type biological analysis device 100 which can be mounted on the ears of a subject, a configuration in which the subject is informed of the average blood pressure Pave by sound is particularly appropriate. The subject may not necessarily be informed of the average blood pressure Pave. For example, the average blood pressure Pave calculated by the biological analysis device 100 may be transmitted from a communication network to another communication device. The average blood pressure Pave may be stored in a portable recording medium detachably mounted on the storage device 22 of the biological analysis device 100 or the biological analysis device 100.

(7) The biological analysis device 100 according to each of the above-described embodiments is realized in cooperation with the control device 21 and a program, as exemplified above. The program according to a preferred aspect of the invention can be provided in a form stored a recording medium which can be read by the computer to be installed on the computer. The program stored in a recording medium included in a delivery server can also be provided to a computer in a form delivered via a communication network. The recording medium is, for example, a non-transitory recording medium. An optical recording medium (optical disc) such as a CD-ROM is a good example, but a recording medium with any known format such as a semiconductor recording medium or a magnetic recording medium can be included. The non-transitory recording medium includes any recording medium removing a transitory and propagating signal, and a volatile recording medium is not excluded.

The entire disclosures of Japanese Patent Application No. 2017-157161, filed Aug. 16, 2017 and Japanese Patent Application No. 2018-104933, filed May 31, 2018 are expressly incorporated by reference herein.

What is claimed is:

1. A biological analysis device comprising:
   a light-emitting unit that radiates a laser beam to a biological body;
   a light-receiving unit that receives laser light reflected inside the biological body; and
   a processor programmed to
      calculate an average blood pressure index related to an average blood pressure of the biological body in accordance with a first preset expression including:
         an average of a blood vessel diameter index related to a blood vessel diameter of the biological body, the blood vessel diameter index including a blood mass index related to a blood mass of the biological body, wherein the blood mass indicates a number of blood cells in a unit volume, and the blood mass index is calculated by the processor according to a second preset expression, and
         an average of a blood flow index related to a blood flow of the biological body, wherein the blood flow index is calculated by the processor according to a third preset expression,
   wherein the second and third preset expressions are different from each other and each include an intensity spectrum related to a frequency of the laser light reflected and received from the inside of the biological body through the radiation of the laser beam, and
   wherein the blood mass index is calculated multiple times during an analysis period, the blood flow index is calculated multiple times during the analysis period, and the blood pressure is calculated only once during the analysis period, such that a single value of the blood pressure obtained during the analysis period is automatically the average blood pressure over the analysis period.

2. The biological analysis device according to claim 1, wherein the average of the blood vessel diameter index is obtained by averaging the blood vessel diameter indexes during the analysis period, and the average of the blood flow index is obtained by averaging the blood flow indexes during the analysis period.

3. The biological analysis device according to claim 2, wherein, when $M_{ave}$ is the average of the blood mass indexes and $F_{ave}$ is the average of the blood flow indexes, the average blood pressure index is calculated in accordance with the first preset expression which is $F_{ave}/M_{ave}^{4/3}$.

4. The biological analysis device according to claim 1, wherein the biological analysis device is worn on an upper arm or a wrist of the biological body.

5. The biological analysis device according to claim 1, wherein the processor is programmed to
calculate the blood vessel diameter index and the blood flow index using a detection signal indicating a light reception level by the light-receiving unit.

6. The biological analysis device according to claim 5, wherein the processor is programmed to
calculate the blood mass index by integrating an intensity of each frequency in the intensity spectrum related to a frequency of the detection signal in a predetermined frequency range.

7. The biological analysis device according to claim 5, wherein the processor is programmed to
calculate the blood flow index by integrating a product of an intensity of each frequency in the intensity spectrum related to a frequency of the detection signal and a frequency within a predetermined frequency range.

8. A biological analysis method comprising:
radiating a laser beam to a biological body;
receiving laser light reflected inside the biological body; and
calculating an average blood pressure index related to an average blood pressure of the biological body in accordance with a first preset expression including:
an average of a blood vessel diameter index related to a blood vessel diameter of the biological body, the blood vessel diameter index including a blood mass index related to a blood mass of the biological body, wherein the blood mass indicates a number of blood cells in a unit volume, and the blood mass index is calculated according to a second preset expression, and
an average of a blood flow index related to a blood flow of the biological body, wherein the blood flow index is calculated according to a third preset expression,
wherein the second and third preset expressions are different from each other and each include an intensity spectrum related to a frequency of the laser light reflected and received from the inside of the biological body through the radiation of the laser beam, and
wherein of the blood mass index is calculated multiple times during an analysis period, the blood flow index is calculated multiple times during the analysis period, and the blood pressure is calculated only once during the analysis period, such that a single value of the blood pressure obtained during the analysis period is automatically the average blood pressure over the analysis period.

9. A non-transitory computer readable medium storing a program causing a device to:
radiate a laser beam to a biological body;
receive laser light reflected inside the biological body; and
calculate an average blood pressure index related to an average blood pressure of the biological body in accordance with a first preset expression including:
an average of a blood vessel diameter index related to a blood vessel diameter of the biological body, the blood vessel diameter index including a blood mass index related to a blood mass of the biological body, wherein the blood mass indicates a number of blood cells in a unit volume, and the blood mass index is calculated according to a second preset expression, and
an average of a blood flow index related to a blood flow of the biological body, wherein the blood flow index is calculated according to a third preset expression,
wherein the second and third preset expressions are different from each other and each include an intensity spectrum related to a frequency of the laser light reflected and received from the inside of the biological body through the radiation of the laser beam, and
wherein the blood mass index is calculated multiple times during an analysis period, the blood flow index is calculated multiple times during the analysis period, and the blood pressure is calculated only once during the analysis period, such that a single value of the blood pressure obtained during the analysis period is automatically the average blood pressure over the analysis period.

10. The biological analysis device according to claim 1, wherein the blood mass index M is calculated by integrating intensity $G(f)$ of each frequency f in the intensity spectrum in a range between a lower limit $f_L$ and upper limit $f_H$, according to the following expression:

$$M = \frac{\int_{f_L}^{f_H} G(f)df}{\langle I^2 \rangle},$$

, wherein $\langle I^2 \rangle$ is an average intensity over a whole bandwidth of a detection signal or an intensity $G(0)$.

11. The biological analysis device according to claim 1, wherein the blood flow index F is calculated by integrating a product of intensity $G(f)$ of each frequency f in the intensity spectrum and the frequency f in a range between a lower limit $f_L$ and an upper limit $f_H$, according to the following expression:

$$F = \frac{\int_{f_L}^{f_H} f \cdot G(f)df}{\langle I^2 \rangle},$$

, wherein $\langle I^2 \rangle$ is an average intensity over a whole bandwidth of a detection signal or an intensity $G(0)$.

12. The biological analysis device according to claim 1, wherein the processor calculates the blood mass index and the blood flow index prior to calculating the average blood pressure index.

13. The biological analysis device according to claim 1, wherein the average blood pressure index is calculated in accordance with the first preset expression which is $$\frac{\text{the average of the blood flow index}}{\text{the average of the blood mass index}^{4/3}}.$$

14. The biological analysis device according to claim 1, wherein the average of the blood flow index and the average of the blood mass index are calculated respectively by averaging a plurality of values of the blood flow index and by averaging a plurality of values of the blood mass index obtained during the analysis period, and the calculation of the blood pressure is performed only once during the analysis period to obtain the average blood pressure over the analysis period.

\* \* \* \* \*